(12) United States Patent
Holtzman

(10) Patent No.: US 6,225,085 B1
(45) Date of Patent: May 1, 2001

(54) LRSG PROTEIN AND NUCLEIC ACID MOLECULES AND USES THEREFOR

(75) Inventor: Douglas A. Holtzman, Jamaica Plain, MA (US)

(73) Assignee: Millennium BioTherapeutics, Inc., Camgridge, MA (US)

( * ) Notice: Subject to any disclaimer, the term of this patent is extended or adjusted under 35 U.S.C. 154(b) by 0 days.

(21) Appl. No.: 09/063,950

(22) Filed: Apr. 21, 1998

(51) Int. Cl.[7] .............................. C12P 21/06; C12N 1/20; C12N 5/00; C12N 15/00
(52) U.S. Cl. ...................... 435/69.1; 435/320.1; 435/325; 435/252.3
(58) Field of Search ................................ 435/69.1, 320.1, 435/252.3, 325

(56) References Cited

FOREIGN PATENT DOCUMENTS

WO 95/02054    1/1995  (WO).

OTHER PUBLICATIONS

Abdollahi, A. et al., "Identification of a gene containing–zinc–finger motifs based on lost expression in malignantly transformed rat ovarian surface epithelial cells," *Cancer Research*, 57(10):2029–2034 (1997).
Ann, D.K. et al., "The structure and organization of a proline–rich protein gene of a mouse multigene family", *J. Biol. Chem.* 260(29):15863–15872 (1985).
Clements, S. et al., Novel multigene families encoding highly repetitive peptides sequences. Sequence analyses of rat and mouse proline–rich protein cDNAs; *J. Biol. Chem.* 260(25):13471–13477 (1985).
Delhanty, P. et al., "The cloning and expression of the baboon acid–labile subunit of the insulin–like growth factor binding protein complex", *Biochem. Biophys. Res. Commun.* 227(3):897–902 (1996).
Hickey, M.J. et al., "Human platelet Glycoprotein V: characterization of the polypeptide and the related Ib–V–IX receptor system of adhesive, leucine–rich glycoproteins", *Proc. Natl. Acad. Sci. USA*, 90(18):8327–8331 (1993).
Kobe, B. et al., "The leucine–rich repeat: a versatile binding motif", *TIBS*, pp. 415–420 (Oct. 1994).
Lanza, F. et al., "Cloning and characterization of the gene encoding the human platelet glycoprotein V. A member of the leucine–rich glycoprotein family cleaved during thrombin–induced platelet activation", *J. Biol. Chem.*, 268(28):20801–20807 (1993).
Leong, S.R. et al., "Structure and functional expression of the acid–labile subunit of the insulin–like growth factor binding protein complex", *Mol. Endocrinol.*, 6:870–876 (1992).
Ravanat, C. et al., "Gene cloning of rat and mouse platelet glycoprotein V: identification of megakaryocyte–specific promoters and demonstration of functional thrombin cleavage", *Blood*, 89(9):3253–3262 (1997).

Roth, G.J. et al., "Human platelet glycoprotein V: A surface leucine–rich glycoprotein related to adhesion", *Biochem. Biophys. Res. Commun.*, 170(1):153–161 (1990).
Shimomura, T. et al., "Rapid purification and characterization of human platelet glycoprotein V: The amino acid sequence contains leucine–rich repetitive modules as in glycoprotein Ib", *Blood*, 75(12):2349–2356 (1990).
Skorstengaard, Kama et al., "Complete primary structure of bovine plasma fibronectin", *J. Biochem.*, 161:441–453 (1986).
Wang and Goldfarb, "Amino acid residues which distinguish the mitogenic potentials of two FGF receptors", *Oncogene*, 14(15):1767–1778.
EMBL Database Accession No. Z69594 for platelet Glycoprotein V (1997).
GenBank™ Accession No. AA250733 for soares ovary tumor NbHOT homo sapiens cDNA clone IMAGE:724100 3', Unpublished (1995).
GenBank™ Accession No. AA410939 for soares ovary tumor NbHOT homo sapiens cDNA clone 724100 5', Unpublished (1995).
GenBank™ Accession No. AA448630 for soares total fetus Nb2HF8 9w homo sapiens cDNA clone 786040 3', Unpublished (1997).
GenBank™ Accession No. AA448721 for soares total fetus Nb2HF8 9w homo sapiens cDNA clone 786040 5', Unpublished (1997).
GenBank™ Accession No. AA455784 for soares ovary tumor NbHOT homo sapiens cDNA clone IMAGE:809553, Unpublished (1997).
GenBank™ Accession No. M11902 for proline–rich salivary protein, (1985).
GenBank™ Accession No. M12410 for Adenovirus type 12/human recombinant viral DNA, recombination junction (1983).
GenBank™ Accession No. M86826 for human IGF binding protein complex acid–labile subunit a mRNA, complete cds (1992).
GenBank™ Accession No. S83462 for ALS=85 kda insulin–like growth factor binding protein–3 complex acid–labile subuit [baboons, liver, mRNA partial, 1818 nt] (1996).

(List continued on next page.)

*Primary Examiner*—Ponnathapu Achutamurthy
*Assistant Examiner*—M. Monshipouri
(74) *Attorney, Agent, or Firm*—Lahive & Cockfield, LLP

(57) ABSTRACT

Novel LRSG polypeptides, proteins, and nucleic acid molecules are disclosed. In addition to isolated, full-length LRSG proteins, the invention further provides isolated LRSG fusion proteins, antigenic peptides and anti-LRSG antibodies. The invention also provides LRSG nucleic acid molecules, recombinant expression vectors containing a nucleic acid molecule of the invention, host cells into which the expression vectors have been introduced and non-human transgenic animals in which a LRSG gene has been introduced or disrupted. Diagnostic, screening and therapeutic methods utilizing compositions of the invention are also provided.

21 Claims, 3 Drawing Sheets

OTHER PUBLICATIONS

GenBank™ Accession No. U72621 for human Lot1 mRNA, complete cds (1996).

PIR Database Accession No. A24264 for protein–rich protein—mouse (fragment) (1985).

PIR Database Accession No. C29149 for proline–rich protein MP2—mouse (fragment) (1985).

SwissProt Accession No. O02833 for insulin–like growth factor binding protein complex acid labile chain precursor (ALS) (1996).

SwissProt Accession No. P40197 for platelet Glycoprotein V precursor (GPV)(CD42D) (1995).

GeneSeq Database Accession No. V88052 for EST clone DN676 from application WO9845437–A2.

*Figure 1A*

```
GTCGACCCACGCGTCCGGAGCCCGGGGCGGGTGGACGCGGACTCGAACGCAGTTGCTTCGGGACCCAGGACCCCCTCGG    79

GCCCGACCCGCCAGGAAAGACTGAGGCCGCGGCCTGCCCCGCCCGGCTCCCTGCGCCGCCGCCGCCTCCCGGGACAGAA   158

M   C   S   R   V   P   L   L   L   P   L   L   L   L   A   L   G   P     19
    G ATG TGC TCC AGG GTC CCT CTG CTG CTG CCG CTG CTC CTG CTA CTG GCC CTG GGG CCT   216

G   V   Q   G   C   P   S   G   C   Q   C   S   Q   P   Q   T   V   F   C   T    39
  GGG GTG CAG GGC TGC CCA TCC GGC TGC CAG TGC AGC CAG CCA CAG ACA GTC TTC TGC ACT   276

A   R   Q   G   T   T   V   P   R   D   V   P   P   D   T   V   G   L   Y   V    59
  GCC CGC CAG GGG ACC ACG GTG CCC CGA GAC GTG CCA CCC GAC ACG GTG GGG CTG TAC GTC   336

F   E   N   G   I   T   M   L   D   A   G   S   F   A   G   L   P   G   L   Q    79
  TTT GAG AAC GGC ATC ACC ATG CTC GAC GCA GGC AGC TTT GCC GGC CTG CCG GGC CTG CAG   396

L   L   D   L   S   Q   N   Q   I   A   S   L   P   S   G   V   F   Q   P   L    99
  CTC CTG GAC CTG TCA CAG AAC CAG ATC GCC AGC CTG CCC AGC GGG GTC TTC CAG CCA CTC   456

A   N   L   S   N   L   D   L   T   A   N   R   L   H   E   I   T   N   E   T   119
  GCC AAC CTC AGC AAC CTG GAC CTG ACG GCC AAC AGG CTG CAT GAA ATC ACC AAT GAG ACC   516

F   R   G   L   R   R   L   E   R   L   Y   L   G   K   N   R   I   R   H   I   139
  TTC CGT GGC CTG CGG CGC CTC GAG CGC CTC TAC CTG GGC AAG AAC CGC ATC CGC CAC ATC   576

Q   P   G   A   F   D   T   L   D   R   L   L   E   L   K   L   Q   D   N   E   159
  CAG CCT GGT GCC TTC GAC ACG CTC GAC CGC CTC CTG GAG CTC AAG CTG CAG GAC AAC GAG   636

L   R   A   L   P   P   L   R   L   P   R   L   L   L   L   D   L   S   H   N   179
  CTG CGG GCA CTG CCC CCG CTG CGC CTG CCC CGC CTG CTG CTG CTG GAC CTC AGC CAC AAC   696

S   L   L   A   L   E   P   G   I   L   D   T   A   N   V   E   A   L   R   L   199
  AGC CTC CTG GCC CTG GAG CCC GGC ATC CTG GAC ACT GCC AAC GTG GAG GCG CTG CGG CTG   756

A   G   L   G   L   Q   Q   L   D   E   G   L   F   S   R   L   R   N   L   H   219
  GCT GGT CTG GGG CTG CAG CAG CTG GAC GAG GGG CTC TTC AGC CGC TTG CGC AAC CTC CAC   816

D   L   D   V   S   D   N   Q   L   E   R   V   P   P   V   I   R   G   L   R   239
  GAC CTG GAT GTG TCC GAC AAC CAG CTG GAG CGA GTG CCA CCT GTG ATC CGA GGC CTC CGG   876

G   L   T   R   L   R   L   A   G   N   T   R   I   A   Q   L   R   P   E   D   259
  GGC CTG ACG CGC CTG CGG CTG GCC GGC AAC ACC CGC ATT GCC CAG CTG CGG CCC GAG GAC   936

L   A   G   L   A   A   L   Q   E   L   D   V   S   N   L   S   L   Q   A   L   279
  CTG GCC GGC CTG GCT GCC CTG CAG GAG CTG GAT GTG AGC AAC CTA AGC CTG CAG GCC CTG   996

P   G   D   L   S   G   L   F   P   R   L   R   L   L   A   A   R   N   P   299
  CCT GGC GAC CTC TCG GGC CTC TTC CCC CGC CTG CGG CTG CTG GCA GCT GCC CGC AAC CCC  1056

F   N   C   V   C   P   L   S   W   F   G   P   W   V   R   E   S   H   V   T   319
  TTC AAC TGC GTG TGC CCC CTG AGC TGG TTT GGC CCC TGG GTG CGC GAG AGC CAC GTC ACA  1116

L   A   S   P   E   E   T   R   C   H   F   P   P   K   N   A   G   R   L   L   339
  CTG GCC AGC CCT GAG GAG ACG CGC TGC CAC TTC CCG CCC AAG AAC GCT GGC CGG CTG CTC  1176

L   E   L   D   Y   A   D   F   G   C   P   A   T   T   T   T   A   T   V   P   359
  CTG GAG CTT GAC TAC GCC GAC TTT GGC TGC CCA GCC ACC ACC ACC ACA GCC ACA GTG CCC  1236

T   T   R   P   V   V   R   E   P   T   A   L   S   S   S   L   A   P   T   W   379
  ACC ACG AGG CCC GTG GTG CGG GAG CCC ACA GCC TTG TCT TCT AGC TTG GCT CCT ACC TGG  1296
```

*Figure 1B*

| | | | | | | | | | | | | | | | | | | | | |
|---|---|---|---|---|---|---|---|---|---|---|---|---|---|---|---|---|---|---|---|---|
| L | S | P | T | A | P | A | T | E | A | P | S | P | P | S | T | A | P | P | T | 399 |
| CTT | AGC | CCC | ACA | GCG | CCG | GCC | ACT | GAG | GCC | CCC | AGC | CCG | CCC | TCC | ACT | GCC | CCA | CCG | ACT | 1356 |
| V | G | P | V | P | Q | P | Q | D | C | P | P | S | T | C | L | N | G | G | T | 419 |
| GTA | GGG | CCT | GTC | CCC | CAG | CCC | CAG | GAC | TGC | CCA | CCG | TCC | ACC | TGC | CTC | AAT | GGG | GGC | ACA | 1416 |
| C | H | L | G | T | R | H | H | L | A | C | L | C | P | E | G | F | T | G | L | 439 |
| TGC | CAC | CTG | GGG | ACA | CGG | CAC | CAC | CTG | GCG | TGC | TTG | TGC | CCC | GAA | GGC | TTC | ACG | GGC | CTG | 1476 |
| Y | C | E | S | Q | M | G | Q | G | T | R | P | S | P | T | P | V | T | P | R | 459 |
| TAC | TGT | GAG | AGC | CAG | ATG | GGG | CAG | GGG | ACA | CGG | CCC | AGC | CCT | ACA | CCA | GTC | ACG | CCG | AGG | 1536 |
| P | P | R | S | L | T | L | G | I | E | P | V | S | P | T | S | L | R | V | G | 479 |
| CCA | CCA | CGG | TCC | CTG | ACC | CTG | GGC | ATC | GAG | CCG | GTG | AGC | CCC | ACC | TCC | CTG | CGC | GTG | GGG | 1596 |
| L | Q | R | Y | L | Q | G | S | S | V | Q | L | R | S | L | R | L | T | Y | R | 499 |
| CTG | CAG | CGC | TAC | CTC | CAG | GGG | AGC | TCC | GTG | CAG | CTC | AGG | AGC | CTC | CGT | CTC | ACC | TAT | CGC | 1656 |
| N | L | S | G | P | D | K | R | L | V | T | L | R | L | P | A | S | L | A | E | 519 |
| AAC | CTA | TCG | GGC | CCT | GAT | AAG | CGG | CTG | GTG | ACG | CTG | CGA | CTG | CCT | GCC | TCG | CTC | GCT | GAG | 1716 |
| Y | T | V | T | Q | L | R | P | N | A | T | Y | S | V | C | V | M | P | L | G | 539 |
| TAC | ACG | GTC | ACC | CAG | CTG | CGG | CCC | AAC | GCC | ACT | TAC | TCC | GTC | TGT | GTC | ATG | CCT | TTG | GGG | 1776 |
| P | G | R | V | P | E | G | E | E | A | C | G | E | A | H | T | P | P | A | V | 559 |
| CCC | GGG | CGG | GTG | CCG | GAG | GGC | GAG | GAG | GCC | TGC | GGG | GAG | GCC | CAT | ACA | CCC | CCA | GCC | GTC | 1836 |
| H | S | N | H | A | P | V | T | Q | A | R | E | G | N | L | P | L | L | I | A | 579 |
| CAC | TCC | AAC | CAC | GCC | CCA | GTC | ACC | CAG | GCC | CGC | GAG | GGC | AAC | CTG | CCG | CTC | CTC | ATT | GCG | 1896 |
| P | A | L | A | A | V | L | L | A | A | L | A | A | V | G | A | A | Y | C | V | 599 |
| CCC | GCC | CTG | GCC | GCG | GTG | CTC | CTG | GCC | GCG | CTG | GCT | GCG | GTG | GGG | GCA | GCC | TAC | TGT | GTG | 1956 |
| R | R | G | R | A | M | A | A | A | Q | D | K | G | Q | V | G | P | G | A | | 619 |
| CGG | CGG | GGG | CGG | GCC | ATG | GCA | GCA | GCG | GCT | CAG | GAC | AAA | GGG | CAG | GTG | GGG | CCA | GGG | GCT | 2016 |
| G | P | L | E | L | E | G | V | K | V | P | L | E | P | G | P | K | A | T | E | 639 |
| GGG | CCC | CTG | GAA | CTG | GAG | GGA | GTG | AAG | GTC | CCC | TTG | GAG | CCA | GGC | CCG | AAG | GCA | ACA | GAG | 2076 |
| G | G | G | E | A | L | P | S | G | S | E | C | E | V | P | L | M | G | F | P | 659 |
| GGC | GGT | GGA | GAG | GCC | CTG | CCC | AGC | GGG | TCT | GAG | TGT | GAG | GTG | CCA | CTC | ATG | GGC | TTC | CCA | 2136 |
| G | P | G | L | Q | S | P | L | H | A | K | P | Y | I | * | | | | | | 674 |
| GGG | CCT | GGC | CTC | CAG | TCA | CCC | CTC | CAC | GCA | AAG | CCC | TAC | ATC | TAA | | | | | | 2181 |

```
GCCAGAGAGAGACAGGGCAGCTGGGGCCGGGCTCTCAGCCAGTGAGATGGCCAGCCCCCTCCTGCTGCCACACCACGTA      2260

AGTTCTCAGTCCCAACCTCGGGGATGTGTGCAGACAGGGCTGTGTGACCACAGCTGGGCCCTGTTCCCTCTGGACCTCG      2339

GTCTCCTCATCTGTGAGATGCTGTGGCCCAGCTGACGAGCCCTAACGTCCCCAGAACCGAGTGCCTATGAGGACAGTGT      2418

CCGCCCTGCCCTCCGCAACGTGCAGTCCCTGGGCACGGCGGGCCCTGCCATGTGCTGGTAACGCATGCCTGGGCCCTGC      2497

TGGGCTCTCCCACTCCAGGCGGACCCTGGGGGCCAGTGAAGGAAGCTCCCGGAAAGAGCAGAGGGAGAGCGGGTAGGCG      2576

GCTGTGTGACTCTAGTCTTGGCCCCAGGAAGCGAAGGAACAAAAGAAACTGGAAAGGAAGATGCTTTAGGAACATGTTT      2655

TGCTTTTTTAAAATATATATATATTTATAAGAGATCCTTTCCCATTTATTCTGGGAAGATGTTTTTCAAACTCAGAGAC      2734

AAGGACTTTGGTTTTTGTAAGACAAACGATGATATGAAGGCCTTTTGTAAGAAAAAATAAAGATGAAGTGTGAAAAAA      2813

AAAAAAAAAAAAAAAAAAAAAAAAAAAAAGGGCGGCCGC                                             2852
```

*Figure 2*

```
                1                                                          60
LRSG-1          MCSRVPLLLPLLLLL---ALGP-GVQG-------------CPSGCQCS-----QPQTVFC
GPV             M-LRGTLLCAVLGLLR------------------AQPFPCPPACKCVFRDAAQ-----C
IGFBP           MALRKGGLALALLLLSWVALGPRSLEGAEPGTPGEAEGPACPATCACSYDDEVNELSVFC 61                                                         120
LRSG-1          TARQGTTVPR-DVPPDTVGLYVFENGITMLDAGSFAGLPGLQLLDLSQNQIASLPSGVFQ
GPV             SGGDVARISALGLP----------------------TNLTHILLFGMGRGVLQSQSFS
IGFBP           SSRNLTRLPD-GIPGGTQALWLDSNNLSSIPPAAFRNLSSLAFLNLQGGQLGSLEPQALL 121                                                        180
LRSG-1          PLANLSNLDLTANRLHEITNETFRGLRRLERLYLGKNRIRHIQPGAFDTLDRLLELKLQD
GPV             GMTVLQRLMISDSHISAVAPGTFSDLIKLKTLRLSRNKITHLPGALLDKMVLLEQLFLDH
IGFBP           GLENLCHLHLERNQLRSLAVGTFAYTPALALLGLSNNRLSRLEDGLFEGLGNLWDLNLGW 181                                                        240
LRSG-1          NELRALPPLRLPRLLLLD---LSHNSLLALEPGILDT-ANVEALRLAGLGLQQLDEGLFS
GPV             NALRGIDQNMFQKLVNLQELALNQNQLDFLPASLFTNLENLKLLDLSGNNLTHLPKGLLG
IGFBP           NSLAVLPDAAFRGLGGLRELVLAGNRLAYLQPALFSGLAELRELDLSRNLRAIKANVFA 241                                                        300
LRSG-1          RLRNLHDLDVSDNQLERVPP-VIRGLRGLTRLRLAGNTRIAQLRPEDLAGLAALQELDVS
GPV             AQAKLERLLLHSNRLVSLDSGLLNSLGALTELQFH-RNHIRSIAPGAFDRLPNLSSLTLS
IGFBP           QLPRLQKLYLDRNLIAAVAPGAFLGLKALRWLDLS-HNRVAGLLEDTFPGLLGLRVLRLS 301                                                        360
LRSG-1          NLSLQALPGDLSGLFPRLRLLAAARNPFNCVCPLSWFGPWVRESHVTLASPEETRCHFPP
GPV             RNHLAFLPSALFLHSHNLTLLTLFENPLAEL-PGVLFGEMGGLQELWL-----NRTQL--
IGFBP           HNAIASLRPRTFEDLHFLEELQLGHNRIRQL-AERSFEGLGQLEVLTL-----DHNQLQE 361                                                        420
LRSG-1          KNAGRLL--LELDYADFG--CPATTTTATVPTTRPVVREPTALSSSLAPTWLSPTA-PAT
GPV             --------------------RTLPAAAFRNLSRLRYLGVTLSPRLSA--LPQGAFQGL
IGFBP           VKVGAFLGLTNVAVMNLSGNCLRNLPEQVFRGLGKLHSLHLE-GSCLGR--IRPHTFAGL

421              *    *    *           * *    *480
LRSG-1          EAPSPPSTAPPTVGPVPQPQDCPPSTCLNGGTCHLG---TRHHLACLCPEGFTGLYCES-
GPV             GELQVLALHSNGLTALPDGL------LRGLGKLRQVSLRRNRLRALPRALFRNLSSLES
IGFBP           SGLRRLFLKDNGLVGIEEQS-------LWGLAELLELDLTSNQLTHLPHQLFQGLGKLEY 481                                                        540
LRSG-1          -QMGQGTRPS-PTPVTPRPPRSLTLGIEPVSPTSLRVGLQRYLQGSSVQLRSLRLTYRNL
GPV             VQLDHNQLETLPGDVFGALPRLTEVLLGHNSWRCDCG-LGPFLG-------WLR-QHLGL
IGFBP           LLLSHNRLAELPADALGPLQRAFWLDVSHNRLEALPGSLLASLG-------RLR--YLNL 541                                                        600
LRSG-1          SGPDKRLVTLRLPASLAEYTVTQLRPNATYSVCVMPLGPGRVPEGEEACGEAHTPPAVHS
GPV             VGGEEPPRCAG-PGAHAGLPLWALPGGD--AECPGPRGPPPRPAADSSSEAPVHPALAPN
IGFBP           R--NNSLRTFT-PQPPGLERLW-LEGNP--WDCSCPLKALRDFALQNPSAVPR-------

601                                                        660
LRSG-1          NHAP------VTQAREGNLPLLIAPALAAVLLAALAAVGAAYCVRRGRAMAAAAQDKGQV
GPV             SSEPWVWAQPVTTGKGQDHSPFWGFYFLLLAVQAMITVIIVFAMIK--------------
IGFBP           ------FVQAICEG-DDCQPPVYTYNNITCASPPEVAGLDL------------------

661                                                        718
LRSG-1          GPGAGPLELEGVKVPLEPGPKATEGGGEALPSGSECEVPLMGFPGPGLQSPLHAKPYI
GPV             ---IGQLFRKLIRER-ALG---------------------------------------
IGFBP           --------RDLGEAHFAPC---------------------------------------
```

SEQUENCE LISTING

<160> NUMBER OF SEQ ID NOS: 9

<210> SEQ ID NO 1
<211> LENGTH: 2852
<212> TYPE: DNA
<213> ORGANISM: Homo sapiens
<220> FEATURE:
<221> NAME/KEY: CDS
<222> LOCATION: (160)..(2178)

<400> SEQUENCE: 1

```
gtcgacccac gcgtccggag cccggggcgg gtggacgcgg actcgaacgc agttgcttcg      60
ggacccagga cccctcgggg cccgacccgc caggaaagac tgaggccgcg gcctgccccg     120 ccggctccc tgcgccgccg ccgcctcccg ggacagaag atg tgc tcc agg gtc         174
                                         Met Cys Ser Arg Val
                                          1               5 cct ctg ctg ctg ccg ctg ctc ctg cta ctg gcc ctg ggg cct ggg gtg       222
Pro Leu Leu Leu Pro Leu Leu Leu Leu Leu Ala Leu Gly Pro Gly Val
             10                  15                  20 cag ggc tgc cca tcc ggc tgc cag tgc agc cag cca cag aca gtc ttc       270
Gln Gly Cys Pro Ser Gly Cys Gln Cys Ser Gln Pro Gln Thr Val Phe
         25                  30                  35 tgc act gcc cgc cag ggg acc acg gtg ccc cga gac gtg cca ccc gac       318
Cys Thr Ala Arg Gln Gly Thr Thr Val Pro Arg Asp Val Pro Pro Asp
     40                  45                  50 acg gtg ggg ctg tac gtc ttt gag aac ggc atc acc atg ctc gac gca       366
Thr Val Gly Leu Tyr Val Phe Glu Asn Gly Ile Thr Met Leu Asp Ala
 55                  60                  65 ggc agc ttt gcc ggc ctg ccg ggc ctg cag ctc ctg gac ctg tca cag       414
Gly Ser Phe Ala Gly Leu Pro Gly Leu Gln Leu Leu Asp Leu Ser Gln
 70                  75                  80                  85 aac cag atc gcc agc ctg ccc agc ggg gtc ttc cag cca ctc gcc aac       462
Asn Gln Ile Ala Ser Leu Pro Ser Gly Val Phe Gln Pro Leu Ala Asn
             90                  95                 100 ctc agc aac ctg gac ctg acg gcc aac agg ctg cat gaa atc acc aat       510
Leu Ser Asn Leu Asp Leu Thr Ala Asn Arg Leu His Glu Ile Thr Asn
        105                 110                 115 gag acc ttc cgt ggc ctg cgg cgc ctc gag cgc ctc tac ctg ggc aag       558
Glu Thr Phe Arg Gly Leu Arg Arg Leu Glu Arg Leu Tyr Leu Gly Lys
    120                 125                 130 aac cgc atc cgc cac atc cag cct ggt gcc ttc gac acg ctc gac cgc       606
Asn Arg Ile Arg His Ile Gln Pro Gly Ala Phe Asp Thr Leu Asp Arg
135                 140                 145 ctc ctg gag ctc aag ctg cag gac aac gag ctg cgg gca ctg ccc ccg       654
Leu Leu Glu Leu Lys Leu Gln Asp Asn Glu Leu Arg Ala Leu Pro Pro
150                 155                 160                 165 ctg cgc ctg ccc cgc ctg ctg ctg gac ctc agc cac aac agc ctc           702
Leu Arg Leu Pro Arg Leu Leu Leu Asp Leu Ser His Asn Ser Leu
                170                 175                 180 ctg gcc ctg gag ccc ggc atc ctg gac act gcc aac gtg gag gcg ctg       750
Leu Ala Leu Glu Pro Gly Ile Leu Asp Thr Ala Asn Val Glu Ala Leu
            185                 190                 195 cgg ctg gct ggt ctg ggg ctg cag cag ctg gac gag ggg ctc ttc agc       798
Arg Leu Ala Gly Leu Gly Leu Gln Gln Leu Asp Glu Gly Leu Phe Ser
        200                 205                 210 cgc ttg cgc aac ctc cac gac ctg gat gtg tcc gac aac cag ctg gag       846
Arg Leu Arg Asn Leu His Asp Leu Asp Val Ser Asp Asn Gln Leu Glu
    215                 220                 225
```

| | | |
|---|---|---|
| cga gtg cca cct gtg atc cga ggc ctc cgg ggc ctg acg cgc ctg cgg<br>Arg Val Pro Pro Val Ile Arg Gly Leu Arg Gly Leu Thr Arg Leu Arg<br>230                  235                  240                  245 | 894 |

```
cga gtg cca cct gtg atc cga ggc ctc cgg ggc ctg acg cgc ctg cgg    894
Arg Val Pro Pro Val Ile Arg Gly Leu Arg Gly Leu Thr Arg Leu Arg
230                 235                 240                 245 ctg gcc ggc aac acc cgc att gcc cag ctg cgg ccc gag gac ctg gcc    942
Leu Ala Gly Asn Thr Arg Ile Ala Gln Leu Arg Pro Glu Asp Leu Ala
                250                 255                 260 ggc ctg gct gcc ctg cag gag ctg gat gtg agc aac cta agc ctg cag    990
Gly Leu Ala Ala Leu Gln Glu Leu Asp Val Ser Asn Leu Ser Leu Gln
            265                 270                 275 gcc ctg cct ggc gac ctc tcg ggc ctc ttc ccc cgc ctg cgg ctg ctg   1038
Ala Leu Pro Gly Asp Leu Ser Gly Leu Phe Pro Arg Leu Arg Leu Leu
        280                 285                 290 gca gct gcc cgc aac ccc ttc aac tgc gtg tgc ccc ctg agc tgg ttt   1086
Ala Ala Ala Arg Asn Pro Phe Asn Cys Val Cys Pro Leu Ser Trp Phe
    295                 300                 305 ggc ccc tgg gtg cgc gag agc cac gtc aca ctg gcc agc cct gag gag   1134
Gly Pro Trp Val Arg Glu Ser His Val Thr Leu Ala Ser Pro Glu Glu
310                 315                 320                 325 acg cgc tgc cac ttc ccg ccc aag aac gct ggc cgg ctg ctc ctg gag   1182
Thr Arg Cys His Phe Pro Pro Lys Asn Ala Gly Arg Leu Leu Leu Glu
                330                 335                 340 ctt gac tac gcc gac ttt ggc tgc cca gcc acc acc acc aca gcc aca   1230
Leu Asp Tyr Ala Asp Phe Gly Cys Pro Ala Thr Thr Thr Thr Ala Thr
            345                 350                 355 gtg ccc acc acg agg ccc gtg gtg cgg gag ccc aca gcc ttg tct tct   1278
Val Pro Thr Thr Arg Pro Val Val Arg Glu Pro Thr Ala Leu Ser Ser
        360                 365                 370 agc ttg gct cct acc tgg ctt agc ccc aca gcg ccg gcc act gag gcc   1326
Ser Leu Ala Pro Thr Trp Leu Ser Pro Thr Ala Pro Ala Thr Glu Ala
    375                 380                 385 ccc agc ccg ccc tcc act gcc cca ccg act gta ggg cct gtc ccc cag   1374
Pro Ser Pro Pro Ser Thr Ala Pro Pro Thr Val Gly Pro Val Pro Gln
390                 395                 400                 405 ccc cag gac tgc cca ccg tcc acc tgc ctc aat ggg ggc aca tgc cac   1422
Pro Gln Asp Cys Pro Pro Ser Thr Cys Leu Asn Gly Gly Thr Cys His
                410                 415                 420 ctg ggg aca cgg cac cac ctg gcg tgc ttg tgc ccc gaa ggc ttc acg   1470
Leu Gly Thr Arg His His Leu Ala Cys Leu Cys Pro Glu Gly Phe Thr
            425                 430                 435 ggc ctg tac tgt gag agc cag atg ggg cag ggg aca cgg ccc agc cct   1518
Gly Leu Tyr Cys Glu Ser Gln Met Gly Gln Gly Thr Arg Pro Ser Pro
        440                 445                 450 aca cca gtc acg ccg agg cca cca cgg tcc ctg acc ctg ggc atc gag   1566
Thr Pro Val Thr Pro Arg Pro Pro Arg Ser Leu Thr Leu Gly Ile Glu
    455                 460                 465 ccg gtg agc ccc acc tcc ctg cgc gtg ggg ctg cag cgc tac ctc cag   1614
Pro Val Ser Pro Thr Ser Leu Arg Val Gly Leu Gln Arg Tyr Leu Gln
470                 475                 480                 485 ggg agc tcc gtg cag ctc agg agc ctc cgt ctc acc tat cgc aac cta   1662
Gly Ser Ser Val Gln Leu Arg Ser Leu Arg Leu Thr Tyr Arg Asn Leu
                490                 495                 500 tcg ggc cct gat aag cgg ctg gtg acg ctg cga ctg cct gcc tcg ctc   1710
Ser Gly Pro Asp Lys Arg Leu Val Thr Leu Arg Leu Pro Ala Ser Leu
            505                 510                 515 gct gag tac acg gtc acc cag ctg cgg ccc aac gcc act tac tcc gtc   1758
Ala Glu Tyr Thr Val Thr Gln Leu Arg Pro Asn Ala Thr Tyr Ser Val
        520                 525                 530 tgt gtc atg cct ttg ggg ccc ggg cgg gtg ccg gag ggc gag gag gcc   1806
Cys Val Met Pro Leu Gly Pro Gly Arg Val Pro Glu Gly Glu Glu Ala
    535                 540                 545
```

-continued

| | |
|---|---|
| tgc ggg gag gcc cat aca ccc cca gcc gtc cac tcc aac cac gcc cca<br>Cys Gly Glu Ala His Thr Pro Pro Ala Val His Ser Asn His Ala Pro<br>550                          555                        560                        565 | 1854 |
| gtc acc cag gcc cgc gag ggc aac ctg ccg ctc ctc att gcg ccc gcc<br>Val Thr Gln Ala Arg Glu Gly Asn Leu Pro Leu Leu Ile Ala Pro Ala<br>                      570                        575                        580 | 1902 |
| ctg gcc gcg gtg ctc ctg gcc gcg ctg gct gcg gtg ggg gca gcc tac<br>Leu Ala Ala Val Leu Leu Ala Ala Leu Ala Ala Val Gly Ala Ala Tyr<br>585                          590                        595 | 1950 |
| tgt gtg cgg cgg ggg cgg gcc atg gca gca gcg gct cag gac aaa ggg<br>Cys Val Arg Arg Gly Arg Ala Met Ala Ala Ala Gln Asp Lys Gly<br>                    600                      605                        610 | 1998 |
| cag gtg ggg cca ggg gct ggg ccc ctg gaa ctg gag gga gtg aag gtc<br>Gln Val Gly Pro Gly Ala Gly Pro Leu Glu Leu Glu Gly Val Lys Val<br>615                          620                        625 | 2046 |
| ccc ttg gag cca ggc ccg aag gca aca gag ggc ggt gga gag gcc ctg<br>Pro Leu Glu Pro Gly Pro Lys Ala Thr Glu Gly Gly Gly Glu Ala Leu<br>630                          635                        640                        645 | 2094 |
| ccc agc ggg tct gag tgt gag gtg cca ctc atg ggc ttc cca ggg cct<br>Pro Ser Gly Ser Glu Cys Glu Val Pro Leu Met Gly Phe Pro Gly Pro<br>                    650                      655                        660 | 2142 |
| ggc ctc cag tca ccc ctc cac gca aag ccc tac atc taagccagag<br>Gly Leu Gln Ser Pro Leu His Ala Lys Pro Tyr Ile<br>665                          670 | 2188 |
| agagacaggg cagctggggc cgggctctca gccagtgaga tggccagccc cctcctgctg | 2248 |
| ccacaccacg taagttctca gtcccaacct cggggatgtg tgcagacagg gctgtgtgac | 2308 |
| cacagctggg ccctgttccc tctggacctc ggtctcctca tctgtgagat gctgtggccc | 2368 |
| agctgacgag ccctaacgtc cccagaaccg agtgcctatg aggacagtgt ccgccctgcc | 2428 |
| ctccgcaacg tgcagtccct gggcacggcg ggccctgcca tgtgctggta acgcatgcct | 2488 |
| gggccctgct gggctctccc actccaggcg gaccctgggg gccagtgaag gaagctcccg | 2548 |
| gaaagagcag agggagagcg ggtaggcggc tgtgtgactc tagtcttggc cccaggaagc | 2608 |
| gaaggaacaa aagaaactgg aaaggaagat gctttaggaa catgttttgc ttttttaaaa | 2668 |
| tatatatata tttataagag atcctttccc atttattctg ggaagatgtt tttcaaactc | 2728 |
| agagacaagg actttggttt ttgtaagaca aacgatgata tgaaggcctt ttgtaagaaa | 2788 |
| aaataaaaga tgaagtgtga aaaaaaaaa aaaaaaaaa aaaaaaaaa aaaagggcgg | 2848 |
| ccgc | 2852 |

<210> SEQ ID NO 2
<211> LENGTH: 673
<212> TYPE: PRT
<213> ORGANISM: Homo sapiens

<400> SEQUENCE: 2

Met Cys Ser Arg Val Pro Leu Leu Pro Leu Leu Leu Leu Leu Leu Ala
1                     5                          10                      15

Leu Gly Pro Gly Val Gln Gly Cys Pro Ser Gly Cys Gln Cys Ser Gln
                      20                        25                        30

Pro Gln Thr Val Phe Cys Thr Ala Arg Gln Gly Thr Thr Val Pro Arg
             35                        40                        45

Asp Val Pro Pro Asp Thr Val Gly Leu Tyr Val Phe Glu Asn Gly Ile
      50                        55                        60

Thr Met Leu Asp Ala Gly Ser Phe Ala Gly Leu Pro Gly Leu Gln Leu
65                     70                        75                      80

```
Leu Asp Leu Ser Gln Asn Gln Ile Ala Ser Leu Pro Ser Gly Val Phe
                 85                  90                  95

Gln Pro Leu Ala Asn Leu Ser Asn Leu Asp Leu Thr Ala Asn Arg Leu
            100                 105                 110

His Glu Ile Thr Asn Glu Thr Phe Arg Gly Leu Arg Arg Leu Glu Arg
            115                 120                 125

Leu Tyr Leu Gly Lys Asn Arg Ile Arg His Ile Gln Pro Gly Ala Phe
        130                 135                 140

Asp Thr Leu Asp Arg Leu Leu Glu Leu Lys Leu Gln Asp Asn Glu Leu
145                 150                 155                 160

Arg Ala Leu Pro Pro Leu Arg Leu Pro Arg Leu Leu Leu Leu Asp Leu
                165                 170                 175

Ser His Asn Ser Leu Leu Ala Leu Glu Pro Gly Ile Leu Asp Thr Ala
            180                 185                 190

Asn Val Glu Ala Leu Arg Leu Ala Gly Leu Gly Leu Gln Gln Leu Asp
        195                 200                 205

Glu Gly Leu Phe Ser Arg Leu Arg Asn Leu His Asp Leu Asp Val Ser
        210                 215                 220

Asp Asn Gln Leu Glu Arg Val Pro Pro Val Ile Arg Gly Leu Arg Gly
225                 230                 235                 240

Leu Thr Arg Leu Arg Leu Ala Gly Asn Thr Arg Ile Ala Gln Leu Arg
                245                 250                 255

Pro Glu Asp Leu Ala Gly Leu Ala Ala Leu Gln Glu Leu Asp Val Ser
            260                 265                 270

Asn Leu Ser Leu Gln Ala Leu Pro Gly Asp Leu Ser Gly Leu Phe Pro
        275                 280                 285

Arg Leu Arg Leu Leu Ala Ala Ala Arg Asn Pro Phe Asn Cys Val Cys
        290                 295                 300

Pro Leu Ser Trp Phe Gly Pro Trp Val Arg Glu Ser His Val Thr Leu
305                 310                 315                 320

Ala Ser Pro Glu Glu Thr Arg Cys His Phe Pro Pro Lys Asn Ala Gly
                325                 330                 335

Arg Leu Leu Leu Glu Leu Asp Tyr Ala Asp Phe Gly Cys Pro Ala Thr
            340                 345                 350

Thr Thr Thr Ala Thr Val Pro Thr Thr Arg Pro Val Val Arg Glu Pro
            355                 360                 365

Thr Ala Leu Ser Ser Ser Leu Ala Pro Thr Trp Leu Ser Pro Thr Ala
        370                 375                 380

Pro Ala Thr Glu Ala Pro Ser Pro Pro Ser Thr Ala Pro Pro Thr Val
385                 390                 395                 400

Gly Pro Val Pro Gln Pro Gln Asp Cys Pro Pro Ser Thr Cys Leu Asn
                405                 410                 415

Gly Gly Thr Cys His Leu Gly Thr Arg His His Leu Ala Cys Leu Cys
            420                 425                 430

Pro Glu Gly Phe Thr Gly Leu Tyr Cys Glu Ser Gln Met Gly Gln Gly
            435                 440                 445

Thr Arg Pro Ser Pro Thr Pro Val Thr Pro Arg Pro Pro Arg Ser Leu
        450                 455                 460

Thr Leu Gly Ile Glu Pro Val Ser Pro Thr Ser Leu Arg Val Gly Leu
465                 470                 475                 480

Gln Arg Tyr Leu Gln Gly Ser Ser Val Gln Leu Arg Ser Leu Arg Leu
                485                 490                 495
```

```
Thr Tyr Arg Asn Leu Ser Gly Pro Asp Lys Arg Leu Val Thr Leu Arg
            500                 505                 510

Leu Pro Ala Ser Leu Ala Glu Tyr Thr Val Thr Gln Leu Arg Pro Asn
        515                 520                 525

Ala Thr Tyr Ser Val Cys Val Met Pro Leu Gly Pro Gly Arg Val Pro
    530                 535                 540

Glu Gly Glu Glu Ala Cys Gly Glu Ala His Thr Pro Pro Ala Val His
545                 550                 555                 560

Ser Asn His Ala Pro Val Thr Gln Ala Arg Glu Gly Asn Leu Pro Leu
                565                 570                 575

Leu Ile Ala Pro Ala Leu Ala Ala Val Leu Leu Ala Ala Leu Ala Ala
            580                 585                 590

Val Gly Ala Ala Tyr Cys Val Arg Arg Gly Arg Ala Met Ala Ala Ala
        595                 600                 605

Ala Gln Asp Lys Gly Gln Val Gly Pro Gly Ala Gly Pro Leu Glu Leu
    610                 615                 620

Glu Gly Val Lys Val Pro Leu Glu Pro Gly Pro Lys Ala Thr Glu Gly
625                 630                 635                 640

Gly Gly Glu Ala Leu Pro Ser Gly Ser Glu Cys Glu Val Pro Leu Met
                645                 650                 655

Gly Phe Pro Gly Pro Gly Leu Gln Ser Pro Leu His Ala Lys Pro Tyr
            660                 665                 670

Ile

<210> SEQ ID NO 3
<211> LENGTH: 2019
<212> TYPE: DNA
<213> ORGANISM: Homo sapiens
<220> FEATURE:
<221> NAME/KEY: CDS
<222> LOCATION: (1)..(2019)

<400> SEQUENCE: 3 atg tgc tcc agg gtc cct ctg ctg ctg ccg ctg ctc ctg cta ctg gcc    48
Met Cys Ser Arg Val Pro Leu Leu Leu Pro Leu Leu Leu Leu Leu Ala
  1               5                  10                  15 ctg ggg cct ggg gtg cag ggc tgc cca tcc ggc tgc cag tgc agc cag    96
Leu Gly Pro Gly Val Gln Gly Cys Pro Ser Gly Cys Gln Cys Ser Gln
             20                  25                  30 cca cag aca gtc ttc tgc act gcc cgc cag ggg acc acg gtg ccc cga   144
Pro Gln Thr Val Phe Cys Thr Ala Arg Gln Gly Thr Thr Val Pro Arg
         35                  40                  45 gac gtg cca ccc gac acg gtg ggg ctg tac gtc ttt gag aac ggc atc   192
Asp Val Pro Pro Asp Thr Val Gly Leu Tyr Val Phe Glu Asn Gly Ile
     50                  55                  60 acc atg ctc gac gca ggc agc ttt gcc ggc ctg ccg ggc ctg cag ctc   240
Thr Met Leu Asp Ala Gly Ser Phe Ala Gly Leu Pro Gly Leu Gln Leu
 65                  70                  75                  80 ctg gac ctg tca cag aac cag atc gcc agc ctg ccc agc ggg gtc ttc   288
Leu Asp Leu Ser Gln Asn Gln Ile Ala Ser Leu Pro Ser Gly Val Phe
                 85                  90                  95 cag cca ctc gcc aac ctc agc aac ctg gac ctg acg gcc aac agg ctg   336
Gln Pro Leu Ala Asn Leu Ser Asn Leu Asp Leu Thr Ala Asn Arg Leu
            100                 105                 110 cat gaa atc acc aat gag acc ttc cgt ggc ctg cgg cgc ctc gag cgc   384
His Glu Ile Thr Asn Glu Thr Phe Arg Gly Leu Arg Arg Leu Glu Arg
        115                 120                 125 ctc tac ctg ggc aag aac cgc atc cgc cac atc cag cct ggt gcc ttc   432
```

```
                                                      -continued

Leu Tyr Leu Gly Lys Asn Arg Ile Arg His Ile Gln Pro Gly Ala Phe
    130                 135                 140 gac acg ctc gac cgc ctc ctg gag ctc aag ctg cag gac aac gag ctg        480
Asp Thr Leu Asp Arg Leu Leu Glu Leu Lys Leu Gln Asp Asn Glu Leu
145                 150                 155                 160 cgg gca ctg ccc ccg ctg cgc ctg ccc cgc ctg ctg ctg gac ctc            528
Arg Ala Leu Pro Pro Leu Arg Leu Pro Arg Leu Leu Leu Asp Leu
                165                 170                 175 agc cac aac agc ctc ctg gcc ctg gag ccc ggc atc ctg gac act gcc        576
Ser His Asn Ser Leu Leu Ala Leu Glu Pro Gly Ile Leu Asp Thr Ala
            180                 185                 190 aac gtg gag gcg ctg cgg ctg gct ggt ctg ggg ctg cag cag ctg gac        624
Asn Val Glu Ala Leu Arg Leu Ala Gly Leu Gly Leu Gln Gln Leu Asp
        195                 200                 205 gag ggg ctc ttc agc cgc ttg cgc aac ctc cac gac ctg gat gtg tcc        672
Glu Gly Leu Phe Ser Arg Leu Arg Asn Leu His Asp Leu Asp Val Ser
210                 215                 220 gac aac cag ctg gag cga gtg cca cct gtg atc cga ggc ctc cgg ggc        720
Asp Asn Gln Leu Glu Arg Val Pro Pro Val Ile Arg Gly Leu Arg Gly
225                 230                 235                 240 ctg acg cgc ctg cgg ctg gcc ggc aac acc cgc att gcc cag ctg cgg        768
Leu Thr Arg Leu Arg Leu Ala Gly Asn Thr Arg Ile Ala Gln Leu Arg
                245                 250                 255 ccc gag gac ctg gcc ggc ctg gct gcc ctg cag gag ctg gat gtg agc        816
Pro Glu Asp Leu Ala Gly Leu Ala Ala Leu Gln Glu Leu Asp Val Ser
            260                 265                 270 aac cta agc ctg cag gcc ctg cct ggc gac ctc tcg ggc ctc ttc ccc        864
Asn Leu Ser Leu Gln Ala Leu Pro Gly Asp Leu Ser Gly Leu Phe Pro
        275                 280                 285 cgc ctg cgg ctg ctg gca gct gcc cgc aac ccc ttc aac tgc gtg tgc        912
Arg Leu Arg Leu Leu Ala Ala Ala Arg Asn Pro Phe Asn Cys Val Cys
290                 295                 300 ccc ctg agc tgg ttt ggc ccc tgg gtg cgc gag agc cac gtc aca ctg        960
Pro Leu Ser Trp Phe Gly Pro Trp Val Arg Glu Ser His Val Thr Leu
305                 310                 315                 320 gcc agc cct gag gag acg cgc tgc cac ttc ccg ccc aag aac gct ggc       1008
Ala Ser Pro Glu Glu Thr Arg Cys His Phe Pro Pro Lys Asn Ala Gly
                325                 330                 335 cgg ctg ctc ctg gag ctt gac tac gcc gac ttt ggc tgc cca gcc acc       1056
Arg Leu Leu Leu Glu Leu Asp Tyr Ala Asp Phe Gly Cys Pro Ala Thr
            340                 345                 350 acc acc aca gcc aca gtg ccc acc acg agg ccc gtg gtg cgg gag ccc       1104
Thr Thr Thr Ala Thr Val Pro Thr Thr Arg Pro Val Val Arg Glu Pro
        355                 360                 365 aca gcc ttg tct tct agc ttg gct cct acc tgg ctt agc ccc aca gcg       1152
Thr Ala Leu Ser Ser Ser Leu Ala Pro Thr Trp Leu Ser Pro Thr Ala
370                 375                 380 ccg gcc act gag gcc ccc agc ccg ccc tcc act gcc cca ccg act gta       1200
Pro Ala Thr Glu Ala Pro Ser Pro Pro Ser Thr Ala Pro Pro Thr Val
385                 390                 395                 400 ggg cct gtc ccc cag ccc cag gac tgc cca ccg tcc acc tgc ctc aat       1248
Gly Pro Val Pro Gln Pro Gln Asp Cys Pro Pro Ser Thr Cys Leu Asn
                405                 410                 415 ggg ggc aca tgc cac ctg ggg aca cgg cac cac ctg gcg tgc ttg tgc       1296
Gly Gly Thr Cys His Leu Gly Thr Arg His His Leu Ala Cys Leu Cys
            420                 425                 430 ccc gaa ggc ttc acg ggc ctg tac tgt gag agc cag atg ggg cag ggg       1344
Pro Glu Gly Phe Thr Gly Leu Tyr Cys Glu Ser Gln Met Gly Gln Gly
        435                 440                 445
```

```
aca cgg ccc agc cct aca cca gtc acg ccg agg cca cca cgg tcc ctg    1392
Thr Arg Pro Ser Pro Thr Pro Val Thr Pro Arg Pro Pro Arg Ser Leu
450                 455                 460 acc ctg ggc atc gag ccg gtg agc ccc acc tcc ctg cgc gtg ggg ctg    1440
Thr Leu Gly Ile Glu Pro Val Ser Pro Thr Ser Leu Arg Val Gly Leu
465                 470                 475                 480 cag cgc tac ctc cag ggg agc tcc gtg cag ctc agg agc ctc cgt ctc    1488
Gln Arg Tyr Leu Gln Gly Ser Ser Val Gln Leu Arg Ser Leu Arg Leu
                485                 490                 495 acc tat cgc aac cta tcg ggc cct gat aag cgg ctg gtg acg ctg cga    1536
Thr Tyr Arg Asn Leu Ser Gly Pro Asp Lys Arg Leu Val Thr Leu Arg
            500                 505                 510 ctg cct gcc tcg ctc gct gag tac acg gtc acc cag ctg cgg ccc aac    1584
Leu Pro Ala Ser Leu Ala Glu Tyr Thr Val Thr Gln Leu Arg Pro Asn
        515                 520                 525 gcc act tac tcc gtc tgt gtc atg cct ttg ggg ccc ggg cgg gtg ccg    1632
Ala Thr Tyr Ser Val Cys Val Met Pro Leu Gly Pro Gly Arg Val Pro
    530                 535                 540 gag ggc gag gag gcc tgc ggg gag gcc cat aca ccc cca gcc gtc cac    1680
Glu Gly Glu Glu Ala Cys Gly Glu Ala His Thr Pro Pro Ala Val His
545                 550                 555                 560 tcc aac cac gcc cca gtc acc cag gcc cgc gag ggc aac ctg ccg ctc    1728
Ser Asn His Ala Pro Val Thr Gln Ala Arg Glu Gly Asn Leu Pro Leu
                565                 570                 575 ctc att gcg ccc gcc ctg gcc gcg gtc ctc ctg gcc gcg ctg gct gcg    1776
Leu Ile Ala Pro Ala Leu Ala Ala Val Leu Leu Ala Ala Leu Ala Ala
            580                 585                 590 gtg ggg gca gcc tac tgt gtg cgg cgg ggg cgg gcc atg gca gca gcg    1824
Val Gly Ala Ala Tyr Cys Val Arg Arg Gly Arg Ala Met Ala Ala Ala
        595                 600                 605 gct cag gac aaa ggg cag gtg ggg cca ggg gct ggg ccc ctg gaa ctg    1872
Ala Gln Asp Lys Gly Gln Val Gly Pro Gly Ala Gly Pro Leu Glu Leu
    610                 615                 620 gag gga gtg aag gtc ccc ttg gag cca ggc ccg aag gca aca gag ggc    1920
Glu Gly Val Lys Val Pro Leu Glu Pro Gly Pro Lys Ala Thr Glu Gly
625                 630                 635                 640 ggt gga gag gcc ctg ccc agc ggg tct gag tgt gag gtg cca ctc atg    1968
Gly Gly Glu Ala Leu Pro Ser Gly Ser Glu Cys Glu Val Pro Leu Met
                645                 650                 655 ggc ttc cca ggg cct ggc ctc cag tca ccc ctc cac gca aag ccc tac    2016
Gly Phe Pro Gly Pro Gly Leu Gln Ser Pro Leu His Ala Lys Pro Tyr
            660                 665                 670 atc                                                                 2019
Ile

<210> SEQ ID NO 4
<211> LENGTH: 560
<212> TYPE: PRT
<213> ORGANISM: Homo sapiens

<400> SEQUENCE: 4

Met Leu Arg Gly Thr Leu Leu Cys Ala Val Leu Gly Leu Leu Arg Ala
  1               5                  10                  15

Gln Pro Phe Pro Cys Pro Pro Ala Cys Lys Cys Val Phe Arg Asp Ala
                 20                  25                  30

Ala Gln Cys Ser Gly Gly Asp Val Ala Arg Ile Ser Ala Leu Gly Leu
             35                  40                  45

Pro Thr Asn Leu Thr His Ile Leu Leu Phe Gly Met Gly Arg Gly Val
         50                  55                  60
```

```
Leu Gln Ser Gln Ser Phe Ser Gly Met Thr Val Leu Gln Arg Leu Met
 65                  70                  75                  80

Ile Ser Asp Ser His Ile Ser Ala Val Ala Pro Gly Thr Phe Ser Asp
                 85                  90                  95

Leu Ile Lys Leu Lys Thr Leu Arg Leu Ser Arg Asn Lys Ile Thr His
            100                 105                 110

Leu Pro Gly Ala Leu Leu Asp Lys Met Val Leu Leu Glu Gln Leu Phe
            115                 120                 125

Leu Asp His Asn Ala Leu Arg Gly Ile Asp Gln Asn Met Phe Gln Lys
        130                 135                 140

Leu Val Asn Leu Gln Glu Leu Ala Leu Asn Gln Asn Gln Leu Asp Phe
145                 150                 155                 160

Leu Pro Ala Ser Leu Phe Thr Asn Leu Glu Asn Leu Lys Leu Leu Asp
                165                 170                 175

Leu Ser Gly Asn Asn Leu Thr His Leu Pro Lys Gly Leu Leu Gly Ala
            180                 185                 190

Gln Ala Lys Leu Glu Arg Leu Leu Leu His Ser Asn Arg Leu Val Ser
            195                 200                 205

Leu Asp Ser Gly Leu Leu Asn Ser Leu Gly Ala Leu Thr Glu Leu Gln
        210                 215                 220

Phe His Arg Asn His Ile Arg Ser Ile Ala Pro Gly Ala Phe Asp Arg
225                 230                 235                 240

Leu Pro Asn Leu Ser Ser Leu Thr Leu Ser Arg Asn His Leu Ala Phe
                245                 250                 255

Leu Pro Ser Ala Leu Phe Leu His Ser His Asn Leu Thr Leu Leu Thr
            260                 265                 270

Leu Phe Glu Asn Pro Leu Ala Glu Leu Pro Gly Val Leu Phe Gly Glu
        275                 280                 285

Met Gly Gly Leu Gln Glu Leu Trp Leu Asn Arg Thr Gln Leu Arg Thr
        290                 295                 300

Leu Pro Ala Ala Ala Phe Arg Asn Leu Ser Arg Leu Arg Tyr Leu Gly
305                 310                 315                 320

Val Thr Leu Ser Pro Arg Leu Ser Ala Leu Pro Gln Gly Ala Phe Gln
                325                 330                 335

Gly Leu Gly Glu Leu Gln Val Leu Ala Leu His Ser Asn Gly Leu Thr
            340                 345                 350

Ala Leu Pro Asp Gly Leu Leu Arg Gly Leu Gly Lys Leu Arg Gln Val
            355                 360                 365

Ser Leu Arg Arg Asn Arg Leu Arg Ala Leu Pro Arg Ala Leu Phe Arg
        370                 375                 380

Asn Leu Ser Ser Leu Glu Ser Val Gln Leu Asp His Asn Gln Leu Glu
385                 390                 395                 400

Thr Leu Pro Gly Asp Val Phe Gly Ala Leu Pro Arg Leu Thr Glu Val
                405                 410                 415

Leu Leu Gly His Asn Ser Trp Arg Cys Asp Cys Gly Leu Gly Pro Phe
            420                 425                 430

Leu Gly Trp Leu Arg Gln His Leu Gly Leu Val Gly Gly Glu Glu Pro
            435                 440                 445

Pro Arg Cys Ala Gly Pro Gly Ala His Ala Gly Leu Pro Leu Trp Ala
        450                 455                 460

Leu Pro Gly Gly Asp Ala Glu Cys Pro Gly Pro Arg Gly Pro Pro Pro
465                 470                 475                 480

Arg Pro Ala Ala Asp Ser Ser Ser Glu Ala Pro Val His Pro Ala Leu
```

```
                        485              490                    495
Ala Pro Asn Ser Ser Glu Pro Trp Val Trp Ala Gln Pro Val Thr Thr
            500                 505                 510
Gly Lys Gly Gln Asp His Ser Pro Phe Trp Gly Phe Tyr Phe Leu Leu
        515                 520                 525
Leu Ala Val Gln Ala Met Ile Thr Val Ile Val Phe Ala Met Ile
    530                 535                 540
Lys Ile Gly Gln Leu Phe Arg Lys Leu Ile Arg Glu Arg Ala Leu Gly
545                 550                 555                 560

<210> SEQ ID NO 5
<211> LENGTH: 605
<212> TYPE: PRT
<213> ORGANISM: Papio hamadryas

<400> SEQUENCE: 5

Met Ala Leu Arg Lys Gly Gly Leu Ala Leu Ala Leu Leu Leu Leu Ser
 1               5                  10                  15
Trp Val Ala Leu Gly Pro Arg Ser Leu Glu Gly Ala Glu Pro Gly Thr
            20                  25                  30
Pro Gly Glu Ala Glu Gly Pro Ala Cys Pro Ala Thr Cys Ala Cys Ser
        35                  40                  45
Tyr Asp Asp Glu Val Asn Glu Leu Ser Val Phe Cys Ser Ser Arg Asn
    50                  55                  60
Leu Thr Arg Leu Pro Asp Gly Ile Pro Gly Gly Thr Gln Ala Leu Trp
65                  70                  75                  80
Leu Asp Ser Asn Asn Leu Ser Ser Ile Pro Pro Ala Ala Phe Arg Asn
                85                  90                  95
Leu Ser Ser Leu Ala Phe Leu Asn Leu Gln Gly Gly Gln Leu Gly Ser
            100                 105                 110
Leu Glu Pro Gln Ala Leu Leu Gly Leu Glu Asn Leu Cys His Leu His
        115                 120                 125
Leu Glu Arg Asn Gln Leu Arg Ser Leu Ala Val Gly Thr Phe Ala Tyr
    130                 135                 140
Thr Pro Ala Leu Ala Leu Leu Gly Leu Ser Asn Asn Arg Leu Ser Arg
145                 150                 155                 160
Leu Glu Asp Gly Leu Phe Glu Gly Leu Gly Asn Leu Trp Asp Leu Asn
                165                 170                 175
Leu Gly Trp Asn Ser Leu Ala Val Leu Pro Asp Ala Ala Phe Arg Gly
            180                 185                 190
Leu Gly Gly Leu Arg Glu Leu Val Leu Ala Gly Asn Arg Leu Ala Tyr
        195                 200                 205
Leu Gln Pro Ala Leu Phe Ser Gly Leu Ala Glu Leu Arg Glu Leu Asp
    210                 215                 220
Leu Ser Arg Asn Ala Leu Arg Ala Ile Lys Ala Asn Val Phe Ala Gln
225                 230                 235                 240
Leu Pro Arg Leu Gln Lys Leu Tyr Leu Asp Arg Asn Leu Ile Ala Ala
                245                 250                 255
Val Ala Pro Gly Ala Phe Leu Gly Leu Lys Ala Leu Arg Trp Leu Asp
            260                 265                 270
Leu Ser His Asn Arg Val Ala Gly Leu Leu Glu Asp Thr Phe Pro Gly
        275                 280                 285
Leu Leu Gly Leu Arg Val Leu Arg Leu Ser His Asn Ala Ile Ala Ser
    290                 295                 300
```

-continued

```
Leu Arg Pro Arg Thr Phe Glu Asp Leu His Phe Leu Glu Glu Leu Gln
305                 310                 315                 320

Leu Gly His Asn Arg Ile Arg Gln Leu Ala Glu Arg Ser Phe Glu Gly
                325                 330                 335

Leu Gly Gln Leu Glu Val Leu Thr Leu Asp His Asn Gln Leu Gln Glu
            340                 345                 350

Val Lys Val Gly Ala Phe Leu Gly Leu Thr Asn Val Ala Val Met Asn
        355                 360                 365

Leu Ser Gly Asn Cys Leu Arg Asn Leu Pro Glu Gln Val Phe Arg Gly
370                 375                 380

Leu Gly Lys Leu His Ser Leu His Leu Glu Gly Ser Cys Leu Gly Arg
385                 390                 395                 400

Ile Arg Pro His Thr Phe Ala Gly Leu Ser Gly Leu Arg Arg Leu Phe
                405                 410                 415

Leu Lys Asp Asn Gly Leu Val Gly Ile Glu Glu Gln Ser Leu Trp Gly
            420                 425                 430

Leu Ala Glu Leu Leu Glu Leu Asp Leu Thr Ser Asn Gln Leu Thr His
        435                 440                 445

Leu Pro His Gln Leu Phe Gln Gly Leu Gly Lys Leu Glu Tyr Leu Leu
    450                 455                 460

Leu Ser His Asn Arg Leu Ala Glu Leu Pro Ala Asp Ala Leu Gly Pro
465                 470                 475                 480

Leu Gln Arg Ala Phe Trp Leu Asp Val Ser His Asn Arg Leu Glu Ala
                485                 490                 495

Leu Pro Gly Ser Leu Leu Ala Ser Leu Gly Arg Leu Arg Tyr Leu Asn
            500                 505                 510

Leu Arg Asn Asn Ser Leu Arg Thr Phe Thr Pro Gln Pro Pro Gly Leu
        515                 520                 525

Glu Arg Leu Trp Leu Glu Gly Asn Pro Trp Asp Cys Ser Cys Pro Leu
    530                 535                 540

Lys Ala Leu Arg Asp Phe Ala Leu Gln Asn Pro Ser Ala Val Pro Arg
545                 550                 555                 560

Phe Val Gln Ala Ile Cys Glu Gly Asp Asp Cys Gln Pro Pro Val Tyr
                565                 570                 575

Thr Tyr Asn Asn Ile Thr Cys Ala Ser Pro Pro Glu Val Ala Gly Leu
            580                 585                 590

Asp Leu Arg Asp Leu Gly Glu Ala His Phe Ala Pro Cys
        595                 600                 605

<210> SEQ ID NO 6
<211> LENGTH: 22
<212> TYPE: PRT
<213> ORGANISM: Artificial Sequence
<220> FEATURE:
<223> OTHER INFORMATION: Xaas at positions 1,3-4,6,8-9,11,14-15 may be
      any amino acid
<220> FEATURE:
<223> OTHER INFORMATION: Xaas at positions 2,5,7,13,17 and 22 may be
      Leu, Ile, Val, Met, Ala, Phe or Tyr
<220> FEATURE:
<223> OTHER INFORMATION: Xaa at postion 10 may be Asn, Cys, or Thr
<220> FEATURE:
<223> OTHER INFORMATION: Xaas at postions 12,16,18-21, if present, may
      be any amino acid
<220> FEATURE:
<223> OTHER INFORMATION: Description of Artificial Sequence: Consensus
      sequence

<400> SEQUENCE: 6
```

-continued

```
Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa
            20
```

<210> SEQ ID NO 7
<211> LENGTH: 46
<212> TYPE: PRT
<213> ORGANISM: Artificial Sequence
<220> FEATURE:
<223> OTHER INFORMATION: Xaas at positions 2-7, 9-15,17-28 and 32-45, if
      present, may be any amino acid
<220> FEATURE:
<223> OTHER INFORMATION: Xaa at postion 30 is any amino acid
<220> FEATURE:
<223> OTHER INFORMATION: Description of Artificial Sequence: Consensus
      sequence

<400> SEQUENCE: 7

```
Cys Xaa Xaa Xaa Xaa Xaa Xaa Cys Xaa Xaa Xaa Xaa Xaa Xaa Cys
 1               5                  10                  15

Xaa Xaa Xaa Xaa Xaa Xaa Xaa Xaa Xaa Xaa Xaa Xaa Cys Xaa Cys Xaa
            20                  25                  30

Xaa Xaa Xaa Xaa Xaa Xaa Xaa Xaa Xaa Xaa Xaa Xaa Xaa Cys
        35                  40                  45
```

<210> SEQ ID NO 8
<211> LENGTH: 38
<212> TYPE: PRT
<213> ORGANISM: Artificial Sequence
<220> FEATURE:
<223> OTHER INFORMATION: Xaas at postions 2-5,7-11,13-18,24, and 26-33
      may be any amino acid
<220> FEATURE:
<223> OTHER INFORMATION: Xaas at positions 19-22 and 24-37, if present,
      may be any amino acid
<220> FEATURE:
<223> OTHER INFORMATION: Description of Artificial Sequence: Consensus
      sequence

<400> SEQUENCE: 8

```
Cys Xaa Xaa Xaa Xaa Cys Xaa Xaa Xaa Xaa Xaa Cys Xaa Xaa Xaa Xaa
 1               5                  10                  15

Xaa Xaa Xaa Xaa Xaa Xaa Cys Xaa Cys Xaa Xaa Xaa Xaa Xaa Xaa Xaa
            20                  25                  30

Xaa Xaa Xaa Xaa Xaa Cys
        35
```

<210> SEQ ID NO 9
<211> LENGTH: 73
<212> TYPE: PRT
<213> ORGANISM: Artificial Sequence
<220> FEATURE:
<223> OTHER INFORMATION: Description of Artificial Sequence: Consensus
      sequence

<400> SEQUENCE: 9

```
Pro Ser Pro Pro Arg Asn Leu Arg Val Thr Asp Ile Thr Pro Thr Ser
 1               5                  10                  15

Ile Thr Val Ser Trp Thr Pro Pro Glu Gly Asn Gly Pro Ile Thr Gly
            20                  25                  30

Tyr Arg Ile Gln Tyr Arg Trp Pro Val Asn Asp Asn Glu Trp Asn Glu
        35                  40                  45
```

```
-continued

Phe Asn Val Pro Arg Thr Thr Asn Ser Tyr Thr Ile Thr Asn Leu Arg
         50                  55                  60

Pro Gly Thr Glu Tyr Glu Phe Arg Val
 65              70
```

US 6,225,085 B1

LRSG PROTEIN AND NUCLEIC ACID MOLECULES AND USES THEREFOR

BACKGROUND OF THE INVENTION

Leucine-rich repeats ("LRRs") were first discovered in leucine-rich α2-glycoprotein, a protein of unknown function from human serum (Takashashi, et al. (1985) *Proc. Natl. Acad. Sci. USA* 82:1906–1910). LRR-containing proteins now represent a diverse group of molecules with differing functions and cellular locations in a variety of organisms (for review see Kobe and Deisenhofer (1994) *Trends Biochem. Sci.* 19:415–421). In particular, LRR-containing proteins are known to be involved in a wide range of functions including protein-protein interactions and signal transduction. For example, adhesive proteins represent the largest group in the LRR superfamily. One family of adhesive LRR-containing proteins includes the small proteoglycans: biglycan, fibromodulin, decorin, lumican, proteoglycan-Lb and osteoinductive factor (OIF, also called osteoglycan). Small proteoglycans bind various components of the extracellular matrix and growth factors. Decorin and fibromodulin regulate collagen-fibril formation; and OIF, in conjunction with the transforming growth factors TGF-β and TGF-β2, induces bone formation.

Another exemplary family of adhesive proteins comprises the proteins of the Ib-V-IX system of platelet glycoproteins. This complex constitutes the receptor for von Willebrand factor and mediates the adhesion of platelets to injured vascular surfaces. The LRR superfamily further contains several families of signal-transducing receptors (e.g., CD 14 and the proto-oncogene trk).

As the name implies, LRRs are distinguished by a consensus sequence consisting predominently of leucines. The consensus sequence compiled from known LRR containing proteins contains leucines or other aliphatic residues at positions 2, 5, 7, 12, 16, 21 and 24, and asparagine, cysteine or threonine at position 10. Most proteins contain exclusively asparagine at position 10.

Given the wide range of important functions of LRR containing proteins, such as protein:protein interactions, matrix association and signal transduction, there exists a need for identifying novel LRR containing proteins as well as for modulators of such molecules for use in regulating a variety of cellular responses.

SUMMARY OF THE INVENTION

The present invention is based, at least in part, on the discovery of nucleic acid and protein molecules, referred to herein as Leucine-rich Surface Glycoprotein ("LRSG") molecules. The LRSG molecules of the present invention are useful as modulating agents in regulating a variety of cellular processes. Accordingly, in one aspect, this invention provides isolated nucleic acid molecules encoding LRSG proteins or biologically active portions thereof, as well as nucleic acid fragments suitable as primers or hybridization probes for the detection of LRSG-encoding nucleic acids.

In one embodiment, a LRSG nucleic acid molecule is 60% homologous to the nucleotide sequence shown in SEQ ID NO:1, SEQ ID NO:3, or the nucleotide sequence of the DNA insert of the plasmid deposited with ATCC as Accession Number 98695, or a complement thereof. In a preferred embodiment, the isolated nucleic acid molecule has the nucleotide sequence shown SEQ ID NO:3, or a complement thereof. In another embodiment, the nucleic acid molecule further comprises nucleotides 1–159 of SEQ ID NO:1. In another embodiment, the nucleic acid molecule further comprises nucleotides 2179–2852 of SEQ ID NO:1. In another preferred embodiment, an isolated nucleic acid molecule has the nucleotide sequence shown in SEQ ID NO:1. In yet another preferred embodiment, an isolated nucleic acid molecule has the nucleotide sequence of the DNA insert of the plasmid deposited with ATCC as Accession Number 98695, or a complement thereof.

In another embodiment, a LRSG nucleic acid molecule includes a nucleotide sequence encoding a protein having an amino acid sequence sufficiently homologous to the amino acid sequence of SEQ ID NO:2. In a preferred embodiment, a LRSG nucleic acid molecule includes a nucleotide sequence encoding a protein having an amino acid sequence at least 60% homologous to the amino acid sequence of SEQ ID NO:2. In another preferred embodiment, an isolated nucleic acid molecule encodes the amino acid sequence of human LRSG. In yet another preferred embodiment, the nucleic acid molecule includes a nucleotide sequence encoding a protein having the amino acid sequence of SEQ ID NO:2.

In another embodiment, an isolated nucleic acid molecule of the present invention encodes a protein, preferably a LRSG protein, which includes a leucine-rich repeat region. In another embodiment, an isolated nucleic acid molecule of the present invention encodes a protein, preferably a LRSG protein, which includes an EGF-like domain. In another embodiment, an isolated nucleic acid molecule of the present invention encodes a protein, preferably a LRSG protein, which includes a fibronectin type III-like (Fn type III) domain. In another embodiment, an isolated nucleic acid molecule of the present invention encodes a protein, preferably a LRSG protein, which includes a leucine-rich repeat region, an EGF-like domain and a FN type III-like domain. In another embodiment, an isolated nucleic acid molecule of the present invention encodes a protein, preferably a LRSG protein, which includes a signal sequence, a leucine-rich repeat region, an EGF-like domain and a FN type III-like domain, and, preferably, is membrane bound. In yet another embodiment, a LRSG nucleic acid molecule encodes a LRSG protein and is a naturally occurring nucleotide sequence.

Another embodiment of the invention features nucleic acid molecules, preferably LRSG nucleic acid molecules, which specifically detect LRSG nucleic acid molecules relative to nucleic acid molecules encoding non-LRSG proteins. For example, in one embodiment, such a nucleic acid molecule is at least 1000, preferably 1000–1250, more preferably 1250–1500, more preferably 1500–1750, and even more preferably 1750–2000 nucleotides in length and hybridizes under stringent conditions to a nucleic acid molecule comprising the nucleotide sequence shown in SEQ ID NO:1, the nucleotide sequence of the DNA insert of the plasmid deposited with ATCC as Accession Number 98695, or a complement thereof.

Another embodiment of the invention provides an isolated nucleic acid molecule which is antisense to the coding strand of a LRSG nucleic acid.

Another aspect of the invention provides a vector comprising a LRSG nucleic acid molecule. In certain embodiments, the vector is a recombinant expression vector. In another embodiment, the invention provides a host cell containing a vector of the invention. The invention also provides a method for producing a protein, preferably a LRSG protein, by culturing in a suitable medium, a host cell of the invention containing a recombinant expression vector such that the protein is produced.

Another aspect of this invention features isolated or recombinant LRSG proteins and polypeptides. In one embodiment, an isolated protein, preferably a LRSG protein, includes a leucine-rich repeat region. In another embodiment, an isolated protein, preferably a LRSG protein, includes an EGF-like domain. In another embodiment, an isolated protein, preferably a LRSG protein, includes a Fn type III-like domain. In another embodiment, an isolated protein, preferably a LRSG protein, includes a leucine-rich repeat region, an EGF-like domain and a FN type III-like domain. In another embodiment, an isolated protein, preferably a LRSG protein, includes a signal sequence, a leucine-rich repeat region, an EGF-like domain and a FN type III-like domain and is, preferably, membrane bound. In another embodiment, an isolated protein, preferably a LRSG protein, has an amino acid sequence sufficiently homologous to the amino acid sequence of SEQ ID NO:2. In a preferred embodiment, a protein, preferably a LRSG protein, has an amino acid sequence at least about 60% homologous to the amino acid sequence of SEQ ID NO:2. In another embodiment, the invention features fragments of the proteins having the amino acid sequence of SEQ ID NO:2, wherein the fragment comprises at least 15 contiguous amino acids of the amino acid sequence of SEQ ID NO:2, or an amino acid or an amino acid sequence encoded by the DNA insert of the plasmid deposited with the ATCC as Accession No. 98695. In another embodiment, a protein, preferably a LRSG protein, has the amino acid sequence of SEQ ID NO:2.

Another embodiment of the invention features an isolated protein, preferably a LRSG protein, which is encoded by a nucleic acid molecule having a nucleotide sequence at least about 60% homologous to a nucleotide sequence of SEQ ID NO:1, SEQ ID NO:3, or a complement thereof. This invention further features an isolated protein, preferably a LRSG protein, which is encoded by a nucleic acid molecule having a nucleotide sequence which hybridizes under stringent hybridization conditions to a nucleic acid molecule comprising the nucleotide sequence of SEQ ID NO:1, SEQ ID NO:3, or a complement thereof.

The proteins of the present invention, preferably LRSG proteins, or biologically active portions thereof, can be operatively linked to a non-LRSG polypeptide to form fusion proteins. The invention further features antibodies, such as monoclonal or polyclonal antibodies, that specifically bind proteins of the invention, preferably LRSG proteins. In addition, the LRSG proteins or biologically active portions thereof can be incorporated into pharmaceutical compositions, which optionally include pharmaceutically acceptable carriers.

In another aspect, the present invention provides a method for detecting LRSG expression in a biological sample by contacting the biological sample with an agent capable of detecting a LRSG nucleic acid molecule, protein or polypeptide such that the presence of a LRSG nucleic acid molecule, protein or polypeptide is detected in the biological sample.

In another aspect, the present invention provides a method for detecting the presence of LRSG activity in a biological sample by contacting the biological sample with an agent capable of detecting an indicator of LRSG activity such that the presence of LRSG activity is detected in the biological sample.

In another aspect, the invention provides a method for modulating LRSG activity comprising contacting a cell capable of expressing LRSG with an agent that modulates LRSG activity such that LRSG activity in the cell is modulated. In one embodiment, the agent inhibits LRSG activity. In another embodiment, the agent stimulates LRSG activity. In one embodiment, the agent is an antibody that specifically binds to a LRSG protein. In another embodiment, the agent modulates expression of LRSG by modulating transcription of a LRSG gene or translation of a LRSG mRNA. In yet another embodiment, the agent is a nucleic acid molecule having a nucleotide sequence that is antisense to the coding strand of a LRSG mRNA or a LRSG gene.

In one embodiment, the methods of the present invention are used to treat a subject having a disorder characterized by aberrant LRSG protein or nucleic acid expression or activity by administering an agent which is a LRSG modulator to the subject. In one embodiment, the LRSG modulator is a LRSG protein. In another embodiment the LRSG modulator is a LRSG nucleic acid molecule. In yet another embodiment, the LRSG modulator is a peptide, peptidomimetic, or other small molecule. In a preferred embodiment, the disorder characterized by aberrant LRSG protein or nucleic acid expression is a proliferative or differentiative disorder.

The present invention also provides a diagnostic assay for identifying the presence or absence of a genetic alteration characterized by at least one of (i) aberrant modification or mutation of a gene encoding a LRSG protein; (ii) mis-regulation of said gene; and (iii) aberrant post-translational modification of a LRSG protein, wherein a wild-type form of said gene encodes an protein with a LRSG activity.

In another aspect the invention provides a method for identifying a compound that binds to or modulates the activity of a LRSG protein, by providing a indicator composition comprising a LRSG protein having LRSG activity, contacting the indicator composition with a test compound, and determining the effect of the test compound on LRSG activity in the indicator composition to identify a compound that modulates the activity of a LRSG protein.

Other features and advantages of the invention will be apparent from the following detailed description and claims.

BRIEF DESCRIPTION OF THE DRAWINGS

FIGS. 1A and 1B depict the cDNA sequence and predicted amino acid sequence of human LRSG-1. The nucleotide sequence corresponds to nucleic acids 1 to 2852 of SEQ ID NO:1. The amino acid sequence corresponds to amino acids 1 to 673 of SEQ ID NO:2.

FIG. 2 depicts an alignment of the amino acid sequence of human LRSG-1 with the amino acid sequences of platelet glycoprotein V precursor (GPV) (SwisProt Accession No. P40197), corresponding to SEQ ID NO:4, and insulin-like growth factor binding protein complex acid labile chain precursor (ALS) (SwisProt Accession No. O02833), corresponding to SEQ ID NO:5. The leucine-rich repeat regions are indicated in italics. The EGF-like domain of LRSG-1 is underlined. The Fn type III-like domain of LRSG-1 is indicated in bold. The conserved cysteine residues of the EGF-like domain of LRSG-1 are indicated with an asterix.

DETAILED DESCRIPTION OF THE INVENTION

The present invention is based on the discovery of novel molecules, referred to herein as LRSG protein and nucleic acid molecules, which comprise a family of molecules having certain conserved structural and functional features. The term "family" when referring to the protein and nucleic acid molecules of the invention is intended to mean two or more proteins or nucleic acid molecules having a common structural domain or motif and having sufficient amino acid or nucleotide sequence homology as defined herein. Such family members can be naturally occurring and can be from either the same or different species. For example, a family can contain a first protein of human origin, as well as other, distinct proteins of human origin or alternatively, can contain homologues of non-human origin. Members of a family may also have common functional characteristics.

In one embodiment, the isolated proteins of the present invention, preferably LRSG proteins, are proteins having an amino acid sequence of about 450–900 amino acid residues in length, preferably about 500–850, more preferably about 550–800, more preferably about 600–750, and even more preferably about 650–700 amino acid residues in length. In one embodiment, an isolated protein of the present invention, preferably a LRSG protein, includes at least one leucine-rich repeat region. As used herein, a leucine-rich repeat (LRR) region is a region of a protein having an amino acid sequence of about 100–600 amino acid residues in length, preferably about 150–550, more preferably about 200–500, more preferably about 300–450 or about 350–400 amino acid residues in length, of which at least about 30–140, preferably about 40–130, more preferably about 50–120, more preferably about 60–90 or about 70–80 amino acid residues are leucine residues. In another embodiment, a LRR region has at least about 10–15% leucine residues, preferably about 15–20% leucine residues, more preferably about 20–25% or about 25–30% leucine resides. Accordingly, in one embodiment, a LRSG protein is human LRSG-1 having a LRR region of about amino acid residues 77–309 of SEQ ID NO:2.

In a preferred embodiment, a leucine-rich repeat region includes about 4–28, preferably about 8–24, more preferably about 10–20, more preferably about 12–18 or about 14–16 leucine-rich repeats. As used herein, a "leucine-rich repeat" ("LRR") is an amino acid motif having an amino acid sequence of about 15–30, preferably about 17–25, and more preferably 19–22 amino acid residues in length, of which about 2–12, preferably 3–10, more preferably 4–9, and more preferably 5–7 amino acid residues are leucine residues. Preferably, a LRR has the consensus sequence X-[LIVMAFY]-X(2)-[LIVMAFY]-X-[LIVMAFY]-X(2)-[NCT]-X(1,2)-[LIVMAFY]-X(2,3)-[LIVMAFY]-X(0–4)-[LIVMAFY], corresponding to SEQ ID NO:6. Accordingly, in one embodiment, a LRSG protein is human LRSG-1 having a LRR region of about amino acid residues 77–309 of SEQ ID NO:2, including about 7 LRRs. LRR 1 is about amino acid residues 77–99 of SEQ ID NO:2. LRR 2 is about amino acid residues 101–123 of SEQ ID NO:2. LRR 3 is about amino acid residues 125–147 of SEQ ID NO:2. LRR 4 is about amino acid residues 149–171 of SEQ ID NO:2. LRR 5 is about amino acid residues 217–238 of SEQ ID NO:2. LRR 6 is about amino acid residues 240–263 of SEQ ID NO:2. LRR 7 is about amino acid residues 289–309 of SEQ ID NO:2.

In another embodiment, a LRSG family member is identified based on the presence of at least one "EGF-like domain" in the protein or corresponding nucleic acid molecule. As used herein, the term "EGF-like domain" refers to an amino acid sequence of at least about 15–55 amino acids in length, preferably about 20–50, more preferably about 25–45, and more preferably 30–40 amino acid residues in length, of which about 3–9, preferably 4–8, more preferably 5–7, and more preferably 6 amino acids are cysteine residues. Preferably, one or more cysteine residues in the EGF-like domain are conserved among LRSG family members or other proteins containing EGF-like domains (i.e., located in the same or similar position as the cysteine residues in other LRSG family members or other proteins containing EGF-like domains). In a preferred embodiment, an "EGF-like domain" has the consensus sequence C-X(0–6)-C-X(0–7)-C-X(0–12)-C-X-C-X(0–14)-C, corresponding to SEQ ID NO:7. In another referred embodiment, an "EGF-like domain" has the consensus sequence C-X(4)-C-X(5)-C-X(6–10)-C-X-C-X(8–12)-C, corresponding to SEQ ID NO:8. Accordingly, in one embodiment, a LRSG protein is human LRSG-1 having an EGF-like domain containing about amino acid residues 409–441 of SEQ ID NO:2. The EGF-like domain is further described in PROSITE Document, Accession No. PDOC00021 (http://expasy.hcuge.ch/cgi-bin/get-prodoc-entry?PDOC00021) and as PROSITE Accession No. PS0022.

In another embodiment, a LRSG family member is identified based on the presence of at least one "fibronectin type III-like domain" ("Fn type III-like domain") in the protein or corresponding nucleic acid molecule. As used herein, the term "Fn type III-like domain" refers to an amino acid sequence of at least about 50–100, preferably about 60–90, more preferably about 70–80, and more preferably at least about 75–76 amino acid residues in length, of which at least about 50–80%, preferably 60–70%, more preferably 65% of the amino acid residues are identical or similar amino acids to the Fn type III consensus domain (SEQ ID NO:9) as shown in Table I below.

TABLE I

| | |
|---|---|
| FN type III - like consensus | PsPPrNLrvtdITpTSItVSWtPPe..gNgpItgYr |
| | P+       L +++++PTS++V    ++      +   +++ R |
| LRSG-1 | PPRSLTLGIEPVSPTSLRVGLQRYLQGSSVQLRSLR |
| FN type III - like consensus | IqYRWpvNdne..WnEfnVPrttnsYTItnLrPGTeYeFRV |
| | ++YR +   +++     +++++P +   +YT+T LRP+   +Y++ V |
| LRSG-1 | LTYR-NLSGPDKRLVTLRLPASLAEYTVTQLRPNATYSVCV |

In a preferred embodiment, the Fn type III-like domain has at least about 60%, preferably at least about 70–80%, 90–95%, 96%, 97%, 98%, or 99% homology to the a Fn type III-like domain of human LRSG-1 having about amino acid residues 460–535 of SEQ ID NO:2. In another embodiment, the Fn type III-like domain is about amino acid residues 460–535 of SEQ ID NO:2. Accordingly, a preferred LRSG protein is a human LRSG-1 having a Fn type III-like domain containing about amino acid residues 460–535 of SEQ ID NO:2. The Fn type III domain is further described in Skorstengaard et al. (1986) Eur. J. Biochem. 161:441–453.

The domains described herein are described according to standard Prosite Signature designation (e.g., all amino acids are indicated according to their universal single letter designation; X designates any amino acid; X(n) designates any n amino acids, e.g., X (2) designates any 2 amino acids; and [LIVM] indicates any one of the amino acids appearing within the brackets, e.g., any one of L, I, V, or M, in the alternative, any one of Leu, Ile, Val, or Met.)

In another embodiment of the invention, a LRSG protein has at least one LRR region, and/or an EGF-like domain, and/or at least one Fn type III-like domain, and, preferably, a signal sequence. In another embodiment, a LRSG has a LRR region, an EGF-like domain, a Fn type III-like domain, and, preferably a signal sequence. As used herein, a "signal sequence" refers to a peptide of about 20–30 amino acid residues in length which occurs at the N-terminus of secretory and integral membrane proteins and which contains a majority of hydrophobic amino acid residues. For example, a signal sequence contains at least about 15–45 amino acid residues, preferably about 20–40 amino acid residues, more preferably about 25–35 amino acid residues, and more preferably about 28–32 amino acid residues, and has at least about 40–70%, preferably about 50–65%, and more preferably about 55–60% hydrophobic amino acid residues (e.g., Alanine, Valine, Leucine, Isoleucine, Phenylalanine, Tyrosine, Tryptophan, or Proline). Such a "signal sequence", also referred to in the art as a "signal peptide", serves to direct a protein containing such a sequence to a lipid bilayer. For example, in one embodiment, a LRSG-1 protein contains a signal sequence of about amino acids 1–23 of SEQ ID NO:2.

In another embodiment of the invention, a LRSG protein has at least one LRR region and/or at least one EGF-like domain, and/or at least one Fn type III-like domain, and a transmembrane domain. As used herein, the term "transmembrane domain" refers to an amino acid sequence having at least about 10, preferably about 13, preferably about 16, more preferably about 19, and even more preferably about 21, 23, 25, 30, 35 or 40 amino acid residues, of which at least about 60–70%, preferably about 80% and more preferably about 90% of the amino acid residues contain non-polar side chains, for example, alanine, valine, leucine, isoleucine, proline, phenylalanine, tryptophan, and methionine. A transmembrane domain is lipophillic in nature. For example, a transmembrane domain can be found at about amino acids 576–599 of SEQ ID NO:2.

Accordingly, one embodiment of the invention features an LRSG protein having a LRR region and/or at least a Fn type III-like domain and a transmembrane domain. Another embodiment features an LRSG protein having a LRR region, and/or at least EGF-like domain, a Fn type III-like domain, and a transmembrane domain. Another embodiment features a LRSG protein having at least a leucine-rich region, an EGF-like domain, a Fn type III-like domain, and a transmembrane domain.

Isolated proteins of the present invention, preferably LRSG proteins, have an amino acid sequence sufficiently homologous to the amino acid sequence of SEQ ID NO:2 or are encoded by a nucleotide sequence sufficiently homologous to SEQ ID NO:1 or SEQ ID NO:3. As used herein, the term "sufficiently homologous" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains have at least about 30–40% homology, preferably 40–50% homology, more preferably 50–60%, and even more preferably 60–70%, 70–80%, or 80–90% homology across the amino acid sequences of the domains and contain at least one and preferably two structural domains or motifs, are defined herein as sufficiently homologous. Furthermore, amino acid or nucleotide sequences which share at least 30–40%, preferably 40–50%, more preferably 50–60%, 60–70%, 70–80%, or 80–90% homology and share a common functional activity are defined herein as sufficiently homologous.

As used interchangeably herein, a "LRSG activity", "biological activity of LRSG" or "functional activity of LRSG", refers to an activity exerted by a LRSG protein, polypeptide or nucleic acid molecule as determined in vivo, or in vitro, according to standard techniques. In one embodiment, a LRSG activity is a direct activity, such as an association with a LRSG-target molecule. As used herein, a "target molecule" is a molecule with which a LRSG protein binds or interacts in nature, such that LRSG-mediated function is achieved. A LRSG target molecule can be a LRSG protein or polypeptide of the present invention or a non-LRSG molecule. For example, a LRSG target molecule can be a non-LRSG protein molecule. Alternatively, a LRSG activity is an indirect activity, such as an activity mediated by interaction of the LRSG protein with a LRSG target molecule such that the target molecule modulates a downstream cellular activity (e.g., interaction of an LRSG molecule with a LRSG target molecule can modulate the activity of that target molecule on an intracellular signaling pathway).

In a preferred embodiment, a LRSG activity is at least one or more of the following activities: (i) interaction of a LRSG protein with a LRSG target molecule; (ii) interaction of a LRSG protein with a LRSG target molecule, wherein the LRSG target is an extracellular matrix protein; (iii) interaction of a LRSG protein with a LRSG target molecule, wherein the LRSG target is an intracellular signaling molecule; and (iv) interaction of a LRSG protein with a LRSG target molecule, wherein the LRSG target is a second molecue on the cell surface which interacts with an intracellular signaling molecule.

In yet another preferred embodiment, a LRSG activity is at least one or more of the following activities: (1) modulation of cellular signal transduction, either in vitro or in vivo; (2) modulatino of protein:protein interactions, either in vitro or in vivo; (3) regulation of cellular proliferation; or (4) regulation of cellular differentiation.

Accordingly, another embodiment of the invention features isolated LRSG proteins and polypeptides having a LRSG activity. Preferred proteins are LRSG proteins having a LRR region and/or at least a Fn type III-like domain and, preferably, a LRSG activity. Additional preferred proteins are LRSG proteins having a LRR region and/or at least an EGF-like domain, a Fn type III-like domain and, preferably, a LRSG activity. In another preferred embodiment, the isolated protein further comprises a signal sequence. In still another preferred embodiment, the isolated protein is a LRSG protein having a LRR region, a Fn type III-like domain, an EGF-like domain, a LRSG activity, preferably an amino acid sequence sufficiently homologous to an amino acid sequence of SEQ ID NO:2, and optionally a signal sequence and/or propeptide.

The human LRSG-1 cDNA, which is approximately 2852 nucleotides in length, encodes a protein which is approximately 673 amino acid residues in length. The human LRSG-1 protein has at least one leucine rich region. A leucine-rich region includes, for example, about amino acids 77–309 of SEQ ID NO:2. The leucine-rich region further contains at least about 7 leucine-rich repeats. Leucine-rich repeats can be found at least about at amino acids 77–99, 101–123, 125–147, 149–171, 217–238, 240–263, and 289–309 of SEQ ID NO:2. The human LRSG-1 protein further has at least an EGF-like domain. An EGF-like domain includes, for example, about amino acids 409–441 of SEQ ID NO:2. The human LRSG-1 protein further has at least a Fn type III-like domain. A Fn type III-like domain includes, for example, about amino acids 460–535 of SEQ ID NO:2. The human LRSG-1 protein is predicted to be a membrane bound protein which further contains a signal sequence at about amino acids 1–23 of SEQ ID NO:2. The prediction of such a signal peptide can be made, for example, utilizing the computer algorithm SIGNALP (Henrik, et al. (1997) *Protein Engineering* 10:1–6). Furthermore, the human LRSG-1 protein is predicted to contain a transmembrane domain at about amino acids 576–599 of SEQ ID NO:2.

Various aspects of the invention are described in further detail in the following subsections:

I. Isolated Nucleic Acid Molecules

One aspect of the invention pertains to isolated nucleic acid molecules that encode LRSG proteins or biologically active portions thereof, as well as nucleic acid fragments sufficient for use as hybridization probes to identify LRSG-encoding nucleic acids (e.g., LRSG mRNA) and fragments for use as PCR primers for the amplification or mutation of LRSG nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated LRSG nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1, the nucleotide sequence of SEQ ID NO:3, or the nucleotide sequence of the DNA insert of the plasmid deposited with ATCC as Accession Number 98695, or a portion thereof, can be isolated using standard molecular biology techniques and the sequence information provided herein. Using all or portion of the nucleic acid sequence of SEQ ID NO:1, the nucleotide sequence of SEQ ID NO:3, or the nucleotide sequence of the DNA insert of the plasmid deposited with ATCC as Accession Number 98695 as a hybridization probe, LRSG nucleic acid molecules can be isolated using standard hybridization and cloning techniques (e.g., as described in Sambrook, J., Fritsh, E. F., and Maniatis, T. *Molecular Cloning. A Laboratory Manual*. 2nd, ed., *Cold Spring Harbor Laboratory*, Cold Spring Harbor Laboratory Press, Cold Spring Harbor, N.Y., 1989).

Moreover, a nucleic acid molecule encompassing all or a portion of SEQ ID NO:1, SEQ ID NO:3, or the nucleotide sequence of the DNA insert of the plasmid deposited with ATCC as Accession Number 98695 can be isolated by the polymerase chain reaction (PCR) using synthetic oligonucleotide primers designed based upon the sequence of SEQ ID NO:1, SEQ ID NO:3, or the nucleotide sequence of the DNA insert of the plasmid deposited with ATCC as Accession Number 98695.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to LRSG nucleotide sequences can be prepared by standard synthetic techniques, e.g., using an automated DNA synthesizer.

In a preferred embodiment, an isolated nucleic acid molecule of the invention comprises the nucleotide sequence shown in SEQ ID NO:1. The sequence of SEQ ID NO:1 corresponds to the human LRSG-1 cDNA. This cDNA comprises sequences encoding the human LRSG-1 protein (i.e., "the coding region", from nucleotides 244–1122), as well as 5' untranslated sequences (nucleotides 1–243) and 3' untranslated sequences (nucleotides 1123–2852). Alternatively, the nucleic acid molecule can comprise only the coding region of SEQ ID NO:1 (e.g., nucleotides 244–1122, corresponding to SEQ ID NO:3).

In another preferred embodiment, an isolated nucleic acid molecule of the invention comprises a nucleic acid molecule which is a complement of the nucleotide sequence shown in SEQ ID NO:1, SEQ ID NO:3, or the nucleotide sequence of the DNA insert of the plasmid deposited with ATCC as Accession Number 98695, or a portion of any of these nucleotide sequences. A nucleic acid molecule which is complementary to the nucleotide sequence shown in SEQ ID NO:1, SEQ ID NO:3, or the nucleotide sequence of the DNA insert of the plasmid deposited with ATCC as Accession Number 98695, is one which is sufficiently complementary to the nucleotide sequence shown in SEQ ID NO:1, SEQ ID NO:3, or the nucleotide sequence of the DNA insert of the plasmid deposited with ATCC as Accession Number 98695, such that it can hybridize to the nucleotide sequence shown in SEQ ID NO:1, SEQ ID NO:3, or the nucleotide sequence of the DNA insert of the plasmid deposited with ATCC as Accession Number 98695, thereby forming a stable duplex.

In still another preferred embodiment, an isolated nucleic acid molecule of the present invention comprises a nucleotide sequence which is at least about 30–35%, preferably about 35–40%, more preferably at least about 40–45%, more preferably at least about 45–50%, and even more preferably at least about 50–55%, 55–60%, 60–65%, 65–70%, 70–75%, 75–80%, 80–85%, 85–90%, or 90–95% or more homologous to nucleotide sequences shown in SEQ ID NO:1, SEQ ID NO:3, or the nucleotide sequence of the DNA insert of the plasmid deposited with ATCC as Accession Number 98695, or a portion of any of these nucleotide sequences.

Moreover, the nucleic acid molecule of the invention can comprise only a portion of the nucleic acid sequence of SEQ ID NO:1, SEQ ID NO:3, or the nucleotide sequence of the DNA insert of the plasmid deposited with ATCC as Accession Number 98695, for example a fragment which can be used as a probe or primer or a fragment encoding a biologically active portion of a LRSG protein. The nucleotide sequence determined from the cloning of the LRSG-1 genes allows for the generation of probes and primers designed for use in identifying and/or cloning other LRSG family members, as well as LRSG homologues from other species.

The probe/primer typically comprises substantially purified oligonucleotide. The oligonucleotide typically comprises a region of nucleotide sequence that hybridizes under stringent conditions to at least about 12, preferably about 25, more preferably about 40, 50 or 75 consecutive nucleotides of a sense sequence of SEQ ID NO:1, SEQ ID NO:3, or the nucleotide sequence of the DNA insert of the plasmid deposited with ATCC as Accession Number 98695, of an anti-sense sequence of SEQ ID NO:1, SEQ ID NO:3, or the nucleotide sequence of the DNA insert of the plasmid deposited with ATCC as Accession Number 98695, or of a naturally occurring mutant of SEQ ID NO:1, SEQ ID NO:3, or the nucleotide sequence of the DNA insert of the plasmid deposited with ATCC as Accession Number 98695. In an exemplary embodiment, a nucleic acid molecule of the present invention comprises a nucleotide sequence which is about 1000, preferably 1000–1250, more preferably 1250–1500, more preferably 1500–1750, and even more preferably 1750–2000 nucleotides in length and hybridizes under stringent hybridization conditions to a nucleic acid molecule of SEQ ID NO:1, SEQ ID NO:3, or the nucleotide sequence of the DNA insert of the plasmid deposited with ATCC as Accession Number 98695.

Probes based on the LRSG nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a LRSG protein, such as by measuring a level of a LRSG-encoding nucleic acid in a sample of cells from a subject e.g., detecting LRSG mRNA levels or determining whether a genomic LRSG gene has been mutated or deleted.

A nucleic acid fragment encoding a "biologically active portion of a LRSG protein" can be prepared by isolating a portion of the nucleotide sequence of SEQ ID NO:1, SEQ ID NO:3, or the nucleotide sequence of the DNA insert of the plasmid deposited with ATCC as Accession Number 98695, which encodes a polypeptide having a LRSG biological activity (the biological activities of the LRSG proteins have previously been described), expressing the encoded portion of the LRSG protein (e.g., by recombinant expression in vitro) and assessing the activity of the encoded portion of the LRSG protein.

The invention further encompasses nucleic acid molecules that differ from the nucleotide sequence shown in SEQ ID NO:1, SEQ ID NO:3, or the nucleotide sequence of the DNA insert of the plasmid deposited with ATCC as Accession Number 98695, due to degeneracy of the genetic code and thus encode the same LRSG proteins as those encoded by the nucleotide sequence shown in SEQ ID NO:1, SEQ ID NO:3, or the nucleotide sequence of the DNA insert of the plasmid deposited with ATCC as Accession Number 98695. In another embodiment, an isolated nucleic acid molecule of the invention has a nucleotide sequence encoding a protein having an amino acid sequence shown in SEQ ID NO:2.

In addition to the LRSG nucleotide sequences shown in SEQ ID NO:1, SEQ ID NO:3, or the nucleotide sequence of the DNA insert of the plasmid deposited with ATCC as Accession Number 98695, it will be appreciated by those skilled in the art that DNA sequence polymorphisms that lead to changes in the amino acid sequences of the LRSG proteins may exist within a population (e.g., the human population). Such genetic polymorphism in the LRSG genes may exist among individuals within a population due to natural allelic variation. As used herein, the terms "gene" and "recombinant gene" refer to nucleic acid molecules comprising an open reading frame encoding a LRSG protein, preferably a mammalian LRSG protein. Such natural allelic variations can typically result in 1–5% variance in the nucleotide sequence of a LRSG gene. Any and all such nucleotide variations and resulting amino acid polymorphisms in LRSG genes that are the result of natural allelic variation and that do not alter the functional activity of a LRSG protein are intended to be within the scope of the invention.

Moreover, nucleic acid molecules encoding other LRSG family members (e.g., LRSG-2), and thus which have a nucleotide sequence which differs from the LRSG-1 sequences of SEQ ID NO:1, SEQ ID NO:3, or the nucleotide sequence of the DNA insert of the plasmid deposited with ATCC as Accession Number 98695 are intended to be within the scope of the invention. For example, a LRSG-2 cDNA can be identified based on the nucleotide sequence of human LRSG-1. Moreover, nucleic acid molecules encoding LRSG proteins from different species, and thus which have a nucleotide sequence which differs from the LRSG sequences of SEQ ID NO:1, SEQ ID NO:3, or the nucleotide sequence of the DNA insert of the plasmid deposited with ATCC as Accession Number 98695 are intended to be within the scope of the invention. For example, an mouse LRSG cDNA can be identified based on the nucleotide sequence of a human LRSG.

Nucleic acid molecules corresponding to natural allelic variants and homologues of the LRSG cDNAs of the invention can be isolated based on their homology to the LRSG nucleic acids disclosed herein using the cDNAs disclosed herein, or a portion thereof, as a hybridization probe according to standard hybridization techniques under stringent hybridization conditions.

Accordingly, in another embodiment, an isolated nucleic acid molecule of the invention is at least 15 nucleotides in length and hybridizes under stringent conditions to the nucleic acid molecule comprising the nucleotide sequence of SEQ ID NO:1, SEQ ID NO:3, or the nucleotide sequence of the DNA insert of the plasmid deposited with ATCC as Accession Number 98695. In other embodiment, the nucleic acid is at least 30, 50, 100, 250 or 500 nucleotides in length. As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 70%, more preferably at least about 80%, even more preferably at least about 85% or 90% homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50–65° C. Preferably, an isolated nucleic acid molecule of the invention that hybridizes under stringent conditions to the sequence of SEQ ID NO:1 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the LRSG sequences that may exist in the population, the skilled artisan will further appreciate that changes can be introduced by mutation into the nucleotide sequences of SEQ ID NO:1, SEQ ID NO:3, or the nucleotide sequence of the DNA insert of the plasmid deposited with ATCC as Accession Number 98695, thereby leading to changes in the amino acid sequence of the encoded LRSG proteins, without altering the functional ability of the LRSG proteins. For example, nucleotide substitutions leading to amino acid substitutions at "non-essential" amino acid residues can be made in the sequence of SEQ ID NO:1, SEQ ID NO:3, or the nucleotide sequence of the DNA insert of the plasmid deposited with ATCC as Accession Number 98695. A "non-essential" amino acid residue is a residue that can be altered from the wild-type sequence of LRSG (e.g., the sequence of SEQ ID NO:2) without altering the biological activity, whereas an "essential" amino acid residue is required for biological activity. For example, amino acid residues that are conserved among the LRSG proteins of the present invention, are predicted to be particularly unameable to alteration (e.g., the ten conserved cysteines involved in forming disulfide linkages or the conserved histidine, aspartate, or serine of the active enzymatic site). Moreover, amino acid residues that are defined by the LRSG EGF-like domain and LRSG Fn type III-like domain signature motifs are particularly unameable to alteration. Furthermore, additional amino acid residues that are conserved between the LRSG proteins of the present invention and other members of the LRR superfamily or protein families containing EGF-like or Fn type III-like domains are not likely to be amenable to alteration.

Accordingly, another aspect of the invention pertains to nucleic acid molecules encoding LRSG proteins that contain changes in amino acid residues that are not essential for activity. Such LRSG proteins differ in amino acid sequence from SEQ ID NO:2 yet retain biological activity. In one embodiment, the isolated nucleic acid molecule comprises a nucleotide sequence encoding a protein, wherein the protein comprises an amino acid sequence at least about 60% homologous to the amino acid sequence of SEQ ID NO:2. Preferably, the protein encoded by the nucleic acid molecule is at least about 65–70% homologous to SEQ ID NO:2, more preferably at least about 75–80% homologous to SEQ ID NO:2, even more preferably at least about 85–90% homologous to SEQ ID NO:2, and most preferably at least about 95% homologous to SEQ ID NO:2.

An isolated nucleic acid molecule encoding a LRSG protein homologous to the protein of SEQ ID NO:2 can be created by introducing one or more nucleotide substitutions, additions or deletions into the nucleotide sequence of SEQ ID NO:1, SEQ ID NO:3, or the nucleotide sequence of the DNA insert of the plasmid deposited with ATCC as Accession Number 98695, such that one or more amino acid substitutions, additions or deletions are introduced into the encoded protein. Mutations can be introduced into SEQ ID NO:1, SEQ ID NO:3, or the nucleotide sequence of the DNA insert of the plasmid deposited with ATCC as Accession Number 98695 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a LRSG protein is preferably replaced with another amino acid residue from the same side chain family. Alternatively, in another embodiment, mutations can be introduced randomly along all or part of a LRSG coding sequence, such as by saturation mutagenesis, and the resultant mutants can be screened for LRSG biological activity to identify mutants that retain activity. Following mutagenesis of SEQ ID NO:1, SEQ ID NO:3, or the nucleotide sequence of the DNA insert of the plasmid deposited with ATCC as Accession Number 98695, the encoded protein can be expressed recombinantly and the activity of the protein can be determined.

In a preferred embodiment, a mutant LRSG protein can be assayed for the ability to (1) modulate cellular signal transduction; (2) modulate protein:protein interactions; (3) regulate cellular proliferation; or (4) regulate cellular differentiation.

In addition to the nucleic acid molecules encoding LRSG proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire LRSG coding strand, or to only a portion thereof. In one embodiment, an antisense nucleic acid molecule is antisense to a "coding region" of the coding strand of a nucleotide sequence encoding LRSG. The term "coding region" refers to the region of the nucleotide sequence comprising codons which are translated into amino acid residues (e.g., the coding region of human LRSG-1 corresponds to SEQ ID NO:3). In another embodiment, the antisense nucleic acid molecule is antisense to a "noncoding region" of the coding strand of a nucleotide sequence encoding LRSG. The term "noncoding region" refers to 5' and 3' sequences which flank the coding region that are not translated into amino acids (i.e., also referred to as 5' and 3' untranslated regions).

Given the coding strand sequences encoding LRSG disclosed herein (e.g., SEQ ID NO:3), antisense nucleic acids of the invention can be designed according to the rules of Watson and Crick base pairing. The antisense nucleic acid molecule can be complementary to the entire coding region of LRSG mRNA, but more preferably is an oligonucleotide which is antisense to only a portion of the coding or noncoding region of LRSG mRNA. For example, the antisense oligonucleotide can be complementary to the region surrounding the translation start site of LRSG mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyl uracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a LRSG protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave LRSG mRNA transcripts to thereby inhibit translation of LRSG mRNA. A ribozyme having specificity for a LRSG-encoding nucleic acid can be designed based upon the nucleotide sequence of a LRSG-1 cDNA disclosed herein (i.e., SEQ ID NO:1, SEQ ID NO:3, or the nucleotide sequence of the DNA insert of the plasmid deposited with ATCC as Accession Number 98695. For example, a derivative of a Tetrahymena L-19 IVS RNA can be constructed in which the nucleotide sequence of the active site is complementary to the nucleotide sequence to be cleaved in a LRSG-encoding mRNA. See, e.g., Cech et al. U.S. Pat. No. 4,987,071; and Cech et al. U.S. Pat. No. 5,116,742. Alternatively, LRSG mRNA can be used to select a catalytic RNA having a specific ribonuclease activity from a pool of RNA molecules. See, e.g., Bartel, D. and Szostak, J. W. (1993) *Science* 261:1411–1418.

Alternatively, LRSG gene expression can be inhibited by targeting nucleotide sequences complementary to the regulatory region of the LRSG (e.g., the LRSG promoter and/or enhancers) to form triple helical structures that prevent transcription of the LRSG gene in target cells. See generally, Helene, C. (1991) *Anticancer Drug Des.* 6(6): 569–84; Helene, C. et al. (1992) *Ann. N.Y. Acad. Sci.* 660:27–36; and Maher, L. J. (1992) *Bioassays* 14(12): 807–15.

In yet another embodiment, the LRSG nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al (1996) *Bioorganic & Medicinal Chemistry* 4 (1):5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. PNAS 93:14670–675.

PNAs of LRSG nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of LRSG nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In another embodiment, PNAs of LRSG can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of LRSG nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. (1996) supra). The synthesis of PNA-DNA chimeras can be performed as described in Hyrup B. (1996) supra and Finn P. J. et al. (1996) *Nucleic Acids Res.* 24 (17):3357–63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag, M. et al. (1989) *Nucleic Acid Res.* 17:5973–88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. el al. (1975) *Bioorganic Med. Chem. Lett.* 5:1119–11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. US.* 86:6553–6556; Lemaitre et al. (1987) *Proc. Natl. Acad. Sci. USA* 84:648–652; PCT Publication No. WO88/09810, published Dec. 15, 1988) or the blood-brain barrier (see, e.g., PCT Publication No. WO89/10134, published Apr. 25, 1988). In addition, oligonucleotides can be modified with hybridization-triggered cleavage agents (See, e.g., Krol et al. (1988) *BioTechniques* 6:958–976) or intercalating agents. (See, e.g., Zon (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

II. Isolated LRSG Proteins and Anti-LRSG Antibodies

One aspect of the invention pertains to isolated LRSG proteins, and biologically active portions thereof, as well as polypeptide fragments suitable for use as immunogens to raise anti-LRSG antibodies. In one embodiment, native LRSG proteins can be isolated from cells or tissue sources by an appropriate purification scheme using standard protein purification techniques. In another embodiment, LRSG proteins are produced by recombinant DNA techniques. Alternative to recombinant expression, a LRSG protein or polypeptide can be synthesized chemically using standard peptide synthesis techniques.

An "isolated" or "purified" protein or biologically active portion thereof is substantially free of cellular material or other contaminating proteins from the cell or tissue source from which the LRSG protein is derived, or substantially free from chemical precursors or other chemicals when chemically synthesized. The language "substantially free of cellular material" includes preparations of LRSG protein in which the protein is separated from cellular components of the cells from which it is isolated or recombinantly produced. In one embodiment, the language "substantially free of cellular material" includes preparations of LRSG protein having less than about 30% (by dry weight) of non-LRSG protein (also referred to herein as a "contaminating protein"), more preferably less than about 20% of non-LRSG protein, still more preferably less than about 10% of non-LRSG protein, and most preferably less than about 5% non-LRSG protein. When the LRSG protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of LRSG protein in which the protein is separated from chemical precursors or other chemicals which are involved in the synthesis of the protein. In one embodiment, the language "substantially free of chemical precursors or other chemicals" includes preparations of LRSG protein having less than about 30% (by dry weight) of chemical precursors or non-LRSG chemicals, more preferably less than about 20% chemical precursors or non-LRSG chemicals, still more preferably less than about 10% chemical precursors or non-LRSG chemicals, and most preferably less than about 5% chemical precursors or non-LRSG chemicals.

Biologically active portions of a LRSG protein include peptides comprising amino acid sequences sufficiently homologous to or derived from the amino acid sequence of the LRSG protein, e.g., the amino acid sequence shown in SEQ ID NO:2, which include less amino acids than the full length LRSG proteins, and exhibit at least one activity of a LRSG protein. Typically, biologically active portions comprise a domain or motif with at least one activity of the LRSG protein. A biologically active portion of a LRSG protein can be a polypeptide which is, for example, 10, 25, 50, 100 or more amino acids in length.

In one embodiment, a biologically active portion of a LRSG protein comprises at least a Fn type III-like domain. In another embodiment, a biologically active portion of a LRSG protein comprises at least an EGF-like domain. In another embodiment, a biologically active portion of a LRSG protein comprises at least a leucine-rich region. In another embodiment, a biologically active portion of a LRSG protein comprises at least one leucine-rich repeat. In another embodiment a biologically active portion of a LRSG protein comprises at least a Fn type III-like domain and an EGF-like domain. In another embodiment, a biologically active portion of a LRSG protein comprises at least a Fn type III-like domain, an EGF-like domain and a transmembrane domain. In another embodiment, a biologically active portion of a LRSG protein comprises at least a leucine rich region, a Fn type III-like domain, an EGF-like domain, and a transmembrane domain.

It is to be understood that a preferred biologically active portion of a LRSG protein of the present invention may contain at least one of the above-identified structural domains. A more preferred biologically active portion of a LRSG protein may contain at least two of the above-identified structural domains. Moreover, other biologically active portions, in which other regions of the protein are deleted, can be prepared by recombinant techniques and evaluated for one or more of the functional activities of a native LRSG protein.

In a preferred embodiment, the LRSG protein has an amino acid sequence shown in SEQ ID NO:2. In other embodiments, the LRSG protein is substantially homologous to SEQ ID NO:2, and retains the functional activity of the protein of SEQ ID NO:2, yet differs in amino acid sequence due to natural allelic variation or mutagenesis, as described in detail in subsection I above. Accordingly, in another embodiment, the LRSG protein is a protein which comprises an amino acid sequence at least about 60% homologous to the amino acid sequence of SEQ ID NO:2 and retains the functional activity of the LRSG proteins of SEQ ID NO:2, respectively. Preferably, the protein is at least about 30–35% homologous to SEQ ID NO:2, more preferably at least about 35–40% homologous to SEQ ID NO:2, even more preferably at least about 40–45% homologous to SEQ ID NO:2, and even more preferably at least about 45–50%, 50–55%, 55–60%, 60–65%, 65–70%, 70–75%, 75–80%, 80–85%, 85–90%, or homologous to SEQ ID NO:2.

To determine the percent homology of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the LRSG amino acid sequence of SEQ ID NO:2 having 673 amino acid residues, at least 88, preferably at least 117, more preferably at least 147, even more preferably at least 176, and even more preferably at least 205, 234 or 264 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., % homology=# of identical positions/total # of positions× 100).

The comparison of sequences and determination of percent homology between two sequences can be accomplished using a mathematical algorithim. A preferred, non-limiting example of a mathematical algorithim utilized for the comparison of sequences is the algorithm of Karlin and Altschul (1990) Proc. Natl. Acad. Sci. USA 87:2264–68, modified as in Karlin and Altschul (1993) Proc. Natl. Acad. Sci. USA 90:5873–77. Such an algorithm is incorporated into the NBLAST and XBLAST programs (version 2.0) of Altschul, et al. (1990) J. Mol. Biol. 215:403–10. BLAST nucleotide searches can be performed with the NBLAST program, score=100, wordlength=12 to obtain nucleotide sequences homologous to LRSG nucleic acid molecules of the invention. BLAST protein searches can be performed with the XBLAST program, score=50, wordlength=3 to obtain amino acid sequences homologous to LRSG protein molecules of the invention. To obtain gapped alignments for comparison purposes, Gapped BLAST can be utilized as described in Altschul et al., (1997) Nucleic Acids Research 25(17):3389–3402. When utilizing BLAST and Gapped BLAST programs, the default parameters of the respective programs (e.g., XBLAST and NBLAST) can be used. See http://www.ncbi.nlm.nih.gov. Another preferred, non-limiting example of a mathematical algorithim utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The invention also provides LRSG chimeric or fusion proteins. As used herein, a LRSG "chimeric protein" or "fusion protein" comprises a LRSG polypeptide operatively linked to a non-LRSG polypeptide. A "LRSG polypeptide" refers to a polypeptide having an amino acid sequence corresponding to LRSG, whereas a "non-LRSG polypeptide" refers to a polypeptide having an amino acid sequence corresponding to a protein which is not substantially homologous to the LRSG protein, e.g., a protein which is different from the LRSG protein and which is derived from the same or a different organism. Within a LRSG fusion protein the LRSG polypeptide can correspond to all or a portion of a LRSG protein. In a preferred embodiment, a LRSG fusion protein comprises at least one biologically active portion of a LRSG protein. In another preferred embodiment, a LRSG fusion protein comprises at least two biologically active portions of a LRSG protein. Within the fusion protein, the term "operatively linked" is intended to indicate that the LRSG polypeptide and the non-LRSG polypeptide are fused in-frame to each other. The non-LRSG polypeptide can be fused to the N-terminus or C-terminus of the LRSG polypeptide.

For example, in one embodiment, the fusion protein is a GST-LRSG fusion protein in which the LRSG sequences are fused to the C-terminus of the GST sequences. Such fusion proteins can facilitate the purification of recombinant LRSG.

In another embodiment, the fusion protein is a LRSG protein containing a heterologous signal sequence at its N-terminus. For example, the native LRSG signal sequence (i.e, about amino acids 1 to 29 of SEQ ID NO:2) can be removed and replaced with a signal sequence from another protein. In certain host cells (e.g., mammalian host cells), expression and/or secretion of LRSG can be increased through use of a heterologous signal sequence.

The LRSG fusion proteins of the invention can be incorporated into pharmaceutical compositions and administered to a subject in vivo. The LRSG fusion proteins can be used to affect the bioavailability of a LRSG target molecule. Use of LRSG fusion proteins may be useful therapeutically for the treatment of proliferative disorders (e.g., prostate cancer). Moreover, the LRSG-fusion proteins of the invention can be used as immunogens to produce anti-LRSG antibodies in a subject, to purify LRSG ligands and in screening assays to identify molecules which inhibit the interaction of LRSG with a LRSG target molecule.

Preferably, a LRSG chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons:1992). Moreover, many expression vectors are commercially available that already encode a fusion moiety (e.g., a GST polypeptide). A LRSG-encoding nucleic acid can be cloned into such an expression vector such that the fusion moiety is linked in-frame to the LRSG protein.

The present invention also pertains to variants of the LRSG proteins which function as either LRSG agonists (mimetics) or as LRSG antagonists. Variants of the LRSG proteins can be generated by mutagenesis, e.g., discrete point mutation or truncation of a LRSG protein. An agonist of the LRSG proteins can retain substantially the same, or a subset, of the biological activities of the naturally occurring form of a LRSG protein. An antagonist of a LRSG protein can inhibit one or more of the activities of the naturally occurring form of the LRSG protein by, for example, competitively inhibiting the protease activity of a LRSG protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the LRSG protein.

In one embodiment, variants of a LRSG protein which function as either LRSG agonists (mimetics) or as LRSG antagonists can be identified by screening combinatorial libraries of mutants, e.g., truncation mutants, of a LRSG protein for LRSG protein agonist or antagonist activity. In one embodiment, a variegated library of LRSG variants is generated by combinatorial mutagenesis at the nucleic acid level and is encoded by a variegated gene library. A variegated library of LRSG variants can be produced by, for example, enzymatically ligating a mixture of synthetic oligonucleotides into gene sequences such that a degenerate set of potential LRSG sequences is expressible as individual polypeptides, or alternatively, as a set of larger fusion proteins (e.g., for phage display) containing the set of LRSG sequences therein. There are a variety of methods which can be used to produce libraries of potential LRSG variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential LRSG sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of a LRSG protein coding sequence can be used to generate a variegated population of LRSG fragments for screening and subsequent selection of variants of a LRSG protein. In one embodiment, a library of coding sequence fragments can be generated by treating a double stranded PCR fragment of a LRSG coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the LRSG protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of LRSG proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recrusive ensemble mutagenesis (REM), a new technique which enhances the frequency of functional mutants in the libraries, can be used in combination with the screening assays to identify LRSG variants (Arkin and Yourvan (1992) *PNAS* 89:7811–7815; Delgrave et al. (1993) *Protein Engineering* 6(3):327–331).

In one embodiment, cell based assays can be exploited to analyze a variegated LRSG library. For example, a library of expression vectors can be transfected into a cell line which ordinarily synthesizes and secretes LRSG. The transfected cells are then cultured such that LRSG and a particular mutant LRSG are secreted and the effect of expression of the mutant on LRSG activity in cell supernatants can be detected, e.g., by any of a number of enzymatic assays. Plasmid DNA can then be recovered from the cells which score for inhibition, or alternatively, potentiation of LRSG activity, and the individual clones further characterized.

An isolated LRSG protein, or a portion or fragment thereof, can be used as an immunogen to generate antibodies that bind LRSG using standard techniques for polyclonal and monoclonal antibody preparation. A full-length LRSG protein can be used or, alternatively, the invention provides antigenic peptide fragments of LRSG for use as immunogens. The antigenic peptide of LRSG comprises at least 8 amino acid residues of the amino acid sequence shown in SEQ ID NO:2 and encompasses an epitope of LRSG such that an antibody raised against the peptide forms a specific immune complex with LRSG. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of LRSG that are located on the surface of the protein, e.g., hydrophilic regions.

A LRSG immunogen typically is used to prepare antibodies by immunizing a suitable subject, (e.g., rabbit, goat, mouse or other mammal) with the immunogen. An appropriate immunogenic preparation can contain, for example, recombinantly expressed LRSG protein or a chemically synthesized LRSG polypeptide. The preparation can further include an adjuvant, such as Freund's complete or incomplete adjuvant, or similar immunostimulatory agent. Immunization of a suitable subject with an immunogenic LRSG preparation induces a polyclonal anti-LRSG antibody response.

Accordingly, another aspect of the invention pertains to anti-LRSG antibodies. The term "antibody" as used herein refers to immunoglobulin molecules and immunologically active portions of immunoglobulin molecules, i.e., molecules that contain an antigen binding site which specifically binds (immunoreacts with) an antigen, such as LRSG. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind LRSG. The term "monoclonal antibody" or "monoclonal antibody composition", as used herein, refers to a population of antibody molecules that contain only one species of an antigen binding site capable of immunoreacting with a particular epitope of LRSG. A monoclonal antibody composition thus typically displays a single binding affinity for a particular LRSG protein with which it immunoreacts.

Polyclonal anti-LRSG antibodies can be prepared as described above by immunizing a suitable subject with a LRSG immunogen. The anti-LRSG antibody titer in the immunized subject can be monitored over time by standard techniques, such as with an enzyme linked immunosorbent assay (ELISA) using immobilized LRSG. If desired, the antibody molecules directed against LRSG can be isolated from the mammal (e.g., from the blood) and further purified by well known techniques, such as protein A chromatography to obtain the IgG fraction. At an appropriate time after immunization, e.g., when the anti-LRSG antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (1981) *J. Immunol.* 127:539–46; Brown et al. (1980) *J. Biol. Chem.* 255:4980–83 ; Yeh et al. (1976) *PNAS* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) Yale *J. Biol. Med.,* 54:387–402; M. L. Gefter et al. (1 977) *Somatic Cell Genet.* 3:231–36). Briefly, an immortal cell line (typically a myeloma) is fused to lymphocytes (typically splenocytes) from a mammal immunized with a LRSG immunogen as described above, and the culture supernatants of the resulting hybridoma cells are screened to identify a hybridoma producing a monoclonal antibody that binds LRSG.

Any of the many well known protocols used for fusing lymphocytes and immortalized cell lines can be applied for the purpose of generating an anti-LRSG monoclonal antibody (see, e.g., G. Galfre et al. (1977) *Nature* 266:55052; Gefter et al. *Somatic Cell Genet.*, cited supra; Lerner, Yale *J Biol. Med*, cited supra; Kenneth, Monoclonal Antibodies, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind LRSG, e.g., using a standard ELISA assay.

Alternative to preparing monoclonal antibody-secreting hybridomas, a monoclonal anti-LRSG antibody can be identified and isolated by screening a recombinant combinatorial immunoglobulin library (e.g., an antibody phage display library) with LRSG to thereby isolate immunoglobulin library members that bind LRSG. Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J* 12:725–734; Hawkins et al. (1992) *J. Mol. Biol.* 226:889–896; Clarkson et al. (1991) *Nature* 352:624–628; Gram et al. (1992) *PNAS* 89:3576–3580; Garrad et al. (1991) *Bio/Technology* 9:1373–1377; Hoogenboom et al. (1991) *Nuc. Acid Res.* 19:4133–4137; Barbas et al. (1991) *PNAS* 88:7978–7982; and McCafferty et al. *Nature* (1990) 348:552–554.

Additionally, recombinant anti-LRSG antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171, 496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041–1043; Liu et al. (1987) *PNAS* 84:3439–3443; Liu et al. (1987) *J. Immunol.* 139:3521–3526; Sun et al. (1987) *PNAS* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison, S. L. (1985) *Science* 229:1202–1207; Oi et al. (1986) *BioTechniques* 4:214; Winter U.S. Pat. No. 5,225,539; Jones et al. (1986) *Nature* 321:552–525; Verhoeyan et al. (1988) *Science* 239:1534; and Beidler et al. (1988) *J. Immunol.* 141:4053–4060.

An anti-LRSG antibody (e.g., monoclonal antibody) can be used to isolate LRSG by standard techniques, such as affinity chromatography or immunoprecipitation. An anti-LRSG antibody can facilitate the purification of natural LRSG from cells and of recombinantly produced LRSG expressed in host cells. Moreover, an anti-LRSG antibody can be used to detect LRSG protein (e.g., in a cellular lysate or cell supernatant) in order to evaluate the abundance and pattern of expression of the LRSG protein. Anti-LRSG antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, -galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I $^{35}$S or $^{3}$H.

III. Recombinant Expression Vectors and Host Cells

Another aspect of the invention pertains to vectors, preferably expression vectors, containing a nucleic acid encoding a LRSG protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., LRSG proteins, mutant forms of LRSG proteins, fusion proteins, etc.).

The recombinant expression vectors of the invention can be designed for expression of LRSG proteins in prokaryotic or eukaryotic cells. For example, LRSG proteins can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes:1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in LRSG activity assays, (e.g., direct assays or competitive assays described in detail below), or to generate antibodies specific for LRSG proteins, for example. In a preferred embodiment, a LRSG fusion protein expressed in a retroviral expression vector of the present invention can be utilized to infect bone marrow cells which are subsequently transplanted into irradiated recipients. The pathology of the subject recipient is then examined after sufficient time has passed (e.g six (6) weeks).

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn 1). This viral polymerase is supplied by host strains BL21 (DE3) or HMS174 (DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111–2118). Such alteration of nucleic acid sequences of the invention can be carried out by standard DNA synthesis techniques.

In another embodiment, the LRSG expression vector is a yeast expression vector. Examples of vectors for expression in yeast *S. cerivisae* include pYepSec 1 (Baldari, et al., (1987) *Embo J.* 6:229–234), pMFa (Kurjan and Herskowitz, (1982) *Cell* 30:933–943), pJRY88 (Schultz et al., (1987) *Gene* 54:113–123), pYES2 (Invitrogen Corporation, San Diego, Calif.), and picZ (InVitrogen Corp, San Diego, Calif.).

Alternatively, LRSG proteins can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual.* 2nd, ed., *Cold Spring Harbor Laboratory*, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *PNAS* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to LRSG mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to host cells into which a recombinant expression vector of the invention has been introduced. The terms "host cell" and "recombinant host cell" are used interchangeably herein. It is understood that such term refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a LRSG protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual.* 2nd, ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding a LRSG protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a LRSG protein. Accordingly, the invention further provides methods for producing a LRSG protein using the host cells of the invention. In one embodiment, the method comprises culturing the host cell of invention (into which a recombinant expression vector encoding a LRSG protein has been introduced) in a suitable medium such that a LRSG protein is produced. In another embodiment, the method further comprises isolating a LRSG protein from the medium or the host cell.

The host cells of the invention can also be used to produce nonhuman transgenic animals. For example, in one embodiment, a host cell of the invention is a fertilized oocyte or an embryonic stem cell into which LRSG-coding sequences have been introduced. Such host cells can then be used to create non-human transgenic animals in which exogenous LRSG sequences have been introduced into their genome or homologous recombinant animals in which endogenous LRSG sequences have been altered. Such animals are useful for studying the function and/or activity of a LRSG and for identifying and/or evaluating modulators of LRSG activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous LRSG gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a LRSG-encoding nucleic acid into the male pronuclei of a fertilized oocyte, e.g., by microinjection, retroviral infection, and allowing the oocyte to develop in a pseudopregnant female foster animal. The LRSG-1cDNA sequence of SEQ ID NO:1 can be introduced as a transgene into the genome of a non-human animal. Alternatively, a nonhuman homologue of a human LRSG-1 gene, such as a mouse or rat LRSG-1 gene, can be used as a transgene. Alternatively, a LRSG-1 gene homologue, such as a LRSG-2 gene can be isolated based on hybridization to the LRSG-1 cDNA sequences of SEQ ID NO:1, SEQ ID NO:3, or the DNA insert of the plasmid deposited with ATCC as Accession Number 98695 (described further in subsection I above) and used as a transgene. Intronic sequences and polyadenylation signals can also be included in the transgene to increase the efficiency of expression of the transgene. A tissue-specific regulatory sequence(s) can be operably linked to a LRSG transgene to direct expression of a LRSG protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., Manipulating the Mouse Embryo, (Cold Spring Harbor Laboratory Press, Cold Spring Harbor, N.Y., 1986). Similar methods are used for production of other transgenic animals. A transgenic founder animal can be identified based upon the presence of a LRSG transgene in its genome and/or expression of LRSG mRNA in tissues or cells of the animals. A transgenic founder animal can then be used to breed additional animals carrying the transgene. Moreover, transgenic animals carrying a transgene encoding a LRSG protein can further be bred to other transgenic animals carrying other transgenes.

To create a homologous recombinant animal, a vector is prepared which contains at least a portion of a LRSG gene into which a deletion, addition or substitution has been introduced to thereby alter, e.g., functionally disrupt, the LRSG gene. The LRSG gene can be a human gene (e.g., the cDNA of SEQ ID NO:3), but more preferably, is a non-human homologue of a human LRSG gene (e.g., a cDNA isolated by stringent hybridization with the nucleotide sequence of SEQ ID NO:1). For example, a mouse LRSG gene can be used to construct a homologous recombination vector suitable for altering an endogenous LRSG gene in the mouse genome. In a preferred embodiment, the vector is designed such that, upon homologous recombination, the endogenous LRSG gene is functionally disrupted (i.e., no longer encodes a functional protein; also referred to as a "knock out" vector). Alternatively, the vector can be designed such that, upon homologous recombination, the endogenous LRSG gene is mutated or otherwise altered but still encodes functional protein (e.g., the upstream regulatory region can be altered to thereby alter the expression of the endogenous LRSG protein). In the homologous recombination vector, the altered portion of the LRSG gene is flanked at its 5' and 3' ends by additional nucleic acid sequence of the LRSG gene to allow for homologous recombination to occur between the exogenous LRSG gene carried by the vector and an endogenous LRSG gene in an embryonic stem cell. The additional flanking LRSG nucleic acid sequence is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced LRSG gene has homologously recombined with the endogenous LRSG gene are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells. A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic non-humans animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *PNAS* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, 1. et al. (1997) *Nature* 385:810–813. In brief, a cell, e.g., a somatic cell, from the transgenic animal can be isolated and induced to exit the growth cycle and enter Go phase. The quiescent cell can then be fused, e.g., through the use of electrical pulses, to an enucleated oocyte from an animal of the same species from which the quiescent cell is isolated. The recontructed oocyte is then cultured such that it develops to morula or blastocyte and then transferred to pseudopregnant female foster animal. The offspring borne of this female foster animal will be a clone of the animal from which the cell, e.g., the somatic cell, is isolated.

IV. Pharmaceutical Compositions

The LRSG nucleic acid molecules, LRSG proteins, and anti-LRSG antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a LRSG protein or anti-LRSG antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The nucleic acid molecules of the invention can be inserted into vectors and used as gene therapy vectors. Gene therapy vectors can be delivered to a subject by, for example, intravenous injection, local administration (see U.S. Pat. No 5,328,470) or by stereotactic injection (see e.g., Chen et al. (1994) *PNAS* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). As described herein, a LRSG protein of the invention has one or more of the following activities: (i) interaction of a LRSG protein with a LRSG target molecule; (ii) interaction of a LRSG protein with a LRSG target molecule, wherein the LRSG target is an extracellular matrix protein; (iii) interaction of a LRSG protein with a LRSG target molecule, wherein the LRSG target is an intracellular signaling molecule; and (iv) interaction of a LRSG protein with a LRSG target molecule, wherein the LRSG target is a second molecue on the cell surface which interacts with an intracellular signaling molecule, and can thus be used in, for example, (1) modulation of cellular signal transduction, either in vitro or in vivo; (2) modulation of protein:protein interaction, either in vitro or in vivo; (3) regulation of cellular proliferation; or (4) regulation of cellular differentiation. The isolated nucleic acid molecules of the invention can be used, for example, to express LRSG protein (e.g., via a recombinant expression vector in a host cell in gene therapy applications), to detect LRSG mRNA (e.g., in a biological sample) or a genetic alteration in a LRSG gene, and to modulate LRSG activity, as described further below. The LRSG proteins can be used to treat disorders characterized by insufficient or excessive production of a LRSG or LRSG target molecules. In addition, the LRSG proteins can be used to screen for naturally occurring LRSG target molecules, to screen for drugs or compounds which modulate LRSG activity, as well as to treat disorders characterized by insufficient or excessive production of LRSG protein or production of LRSG protein forms which have decreased or aberrant activity compared to LRSG wild type protein. Moreover, the anti-LRSG antibodies of the invention can be used to detect and isolate LRSG proteins, regulate the bioavailability of LRSG proteins, and modulate LRSG activity.

Accordingly one embodiment of the present invention involves a method of use (e.g., a diagnostic assay, prognostic assay, or a prophylactic/therapeutic method of treatment) wherein a molecule of the present invention (e.g., a LRSG protein, LRSG nucleic acid, or a LRSG modulator) is used, for example, to diagnose, prognose and/or treat a disease and/or condition in which any of the aforementioned activities (i.e., activities (i)–(vi) and (1)–(4) in the above paragraph) is indicated. In another embodiment, the present invention involves a method of use (e.g., a diagnostic assay, prognostic assay, or a prophylactic/therapeutic method of treatment) wherein a molecule of the present invention (e.g., a LRSG protein, LRSG nucleic acid, or a LRSG modulator)

is used, for example, for the diagnosis, prognosis, and/or treatment of subjects, preferably a human subject, in which any of the aforementioned activities is pathologically perturbed. In a preferred embodiment, the methods of use (e.g., diagnostic assays, prognostic assays, or prophylactic/therapeutic methods of treatment) involve administering to a subject, preferably a human subject, a molecule of the present invention (e.g., a LRSG protein, LRSG nucleic acid, or a LRSG modulator) for the diagnosis, prognosis, and/or therapeutic treatment. In another embodiment, the methods of use (e.g., diagnostic assays, prognostic assays, or prophylactic/therapeutic methods of treatment) involve administering to a human subject a molecule of the present invention (e.g., a LRSG protein, LRSG nucleic acid, or a LRSG modulator).

A. Screening Assays:

The invention provides a method (also referred to herein as a "screening assay") for identifying modulators, i.e., candidate or test compounds or agents (e.g., peptides, peptidomimetics, small molecules or other drugs) which bind to LRSG proteins, have a stimulatory or inhibitory effect on, for example, LRSG expression or LRSG activity, or have a stimulatory or inhibitory effect on, for example, the activity of an LRSG target molecule.

In one embodiment, the invention provides assays for screening candidate or test compounds which are target molecules of a LRSG protein or polypeptide or biologically active portion thereof. In another embodiment, the invention provides assays for screening candidate or test compounds which bind to or modulate the activity of a LRSG protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1 997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223, 409), spores (Ladner U.S. Pat. No. '409), plasmids (Cull et al. (1992) *Proc Natl Acad Sci USA* 89:1865–1869) or on phage (Scott and Smith (1990) *Science* 249:386–390); (Devin (1990) *Science* 249:404–406); (Cwirla et al. (1990) *Proc. Natl. Acad. Sci.* 87:6378–6382); (Felici (1991) *J. Mol. Biol.* 222:301–310); (Ladner supra.).

In one embodiment, an assay is a cell-based assay in which a cell which expresses a LRSG protein or biologically active portion thereof is contacted with a test compound and the ability of the test compound to modulate LRSG activity determined. Determining the ability of the test compound to modulate LRSG activity can be accomplished by monitoring the bioactivity of the LRSG protein or biologically active portion thereof. The cell, for example, can be of mammalian origin or a yeast cell. Determining the ability of the test compound to modulate LRSG activity can be accomplished, for example, by coupling the LRSG protein or biologically active portion thereof with a radioisotope or enzymatic label such that binding of the LRSG protein or biologically active portion thereof to its cognate target molecule can be determined by detecting the labeled LRSG protein or biologically active portion thereof in a complex. For example, compounds (e.g., LRSG protein or biologically active portion thereof) can be labeled with $^{125}I$, $^{35}S$, $^{14}C$, or $^{3}H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound (e.g., LRSG protein or biologically active portion thereof) to interact with its cognate target molecule without the labeling of any of the interactants. For example, a microphysiometer can be used to detect the interaction of a compound with its cognate target molecule without the labeling of either the compound or the receptor. McConnell, H. M. et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between compound and receptor.

In a preferred embodiment, the assay comprises contacting a cell which expresses a LRSG protein or biologically active portion thereof, with a target molecule to form an assay mixture, contacting the assay mixture with a test compound, and determining the ability of the test compound to modulate the activity of the LRSG protein or biologically active portion thereof, wherein determining the ability of the test compound to modulate the activity of the LRSG protein or biologically active portion thereof, comprises determining the ability of the test compound to modulate a biological activity of the LRSG expressing cell (e.g., determining the ability of the test compound to modulate signal transduction or protein:protein interactions).

In another preferred embodiment, the assay comprises contacting a cell which is responsive to a LRSG protein or biologically active portion thereof, with a LRSG protein or biologically-active portion thereof, to form an assay mixture, contacting the assay mixture with a test compound, and determining the ability of the test compound to modulate the activity of the LRSG protein or biologically active portion thereof, wherein determining the ability of the test compound to modulate the activity of the LRSG protein or biologically active portion thereof comprises determining the ability of the test compound to modulate a biological activity of the LRSG-responsive cell (e.g., determining the ability of the test compound to modulate signal transduction or protein:protein interactions).

In another embodiment, an assay is a cell-based assay comprising contacting a cell expressing a LRSG target molecule with a test compound and determining the ability of the test compound to modulate (e.g. stimulate or inhibit) the activity of the LRSG target molecule. Determining the ability of the test compound to modulate the activity of a LRSG target molecule can be accomplished, for example, by determining the ability of the LRSG protein to bind to or interact with the LRSG target molecule.

Determining the ability of the LRSG protein to bind to or interact with a LRSG target molecule can be accomplished by one of the methods described above for determining direct binding. In a preferred embodiment, determining the ability of the LRSG protein to bind to or interact with a LRSG target molecule can be accomplished by determining the activity of the target molecule. For example, the activity of the target molecule can be determined by detecting induction of a cellular second messenger of the target (i.e. intracellular $Ca^{2+}$, diacylglycerol, $IP_3$, etc.), detecting catalytic/enzymatic activity of the target an appropriate substrate, detecting the induction of a reporter gene (comprising a target-responsive regulatory element operatively linked to a nucleic acid encoding a detectable marker, e.g., luciferase), or detecting a target-regulated cellular response, for example, signal transduction or protein:protein interactions.

In yet another embodiment, an assay of the present invention is a cell-free assay in which a LRSG protein or biologically active portion thereof is contacted with a test compound and the ability of the test compound to bind to the LRSG protein or biologically active portion thereof is determined. Binding of the test compound to the LRSG protein can be determined either directly or indirectly as described above. In a preferred embodiment, the assay includes contacting the LRSG protein or biologically active portion thereof with a known compound which binds LRSG (e.g., a LRSG target molecule) to form an assay mixture, contacting the assay mixture with a test compound, and determining the ability of the test compound to interact with a LRSG protein, wherein determining the ability of the test compound to interact with a LRSG protein comprises determining the ability of the test compound to preferentially bind to LRSG or biologically active portion thereof as compared to the known compound.

In another embodiment, the assay is a cell-free assay in which a LRSG protein or biologically active portion thereof is contacted with a test compound and the ability of the test compound to modulate (e.g., stimulate or inhibit) the activity of the LRSG protein or biologically active portion thereof is determined. Determining the ability of the test compound to modulate the activity of a LRSG protein can be accomplished, for example, by determining the ability of the LRSG protein to bind to a LRSG target molecule by one of the methods described above for determining direct binding. Determining the ability of the LRSG protein to bind to a LRSG target molecule can also be accomplished using a technology such as real-time Biomolecular Interaction Analysis (BIA). Sjolander, S. and Urbaniczky, C. (1991) *Anal. Chem.* 63:2338–2345 and Szabo et al. (1995) *Curr. Opin. Struct. Biol.* 5:699–705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In an alternative embodiment, determining the ability of the test compound to modulate the activity of a LRSG protein can be accomplished by determining the ability of the LRSG protein to further modulate the activity of a downstream effector (e.g., a growth factor mediated signal transduction pathway component) of a LRSG target molecule. For example, the activity of the effector molecule on an appropriate target can be determined or the binding of the effector to an appropriate target can be determined as previously described.

In yet another embodiment, the cell-free assay involves contacting a LRSG protein or biologically active portion thereof with a known compound which binds the LRSG protein to form an assay mixture, contacting the assay mixture with a test compound, and determining the ability of the test compound to interact with the LRSG protein, wherein determining the ability of the test compound to interact with the LRSG protein comprises determining the ability of the LRSG protein to preferentially bind to or modulate the activity of a LRSG target molecule.

The cell-free assays of the present invention are amenable to use of both soluble and/or membrane-bound forms of isolated proteins (e.g. LRSG proteins or biologically active portions thereof or receptors to which LRSG targets bind). In the case of cell-free assays in which a membrane-bound form an isolated protein is used (e.g., a cell surface receptor) it may be desirable to utilize a solubilizing agent such that the membrane-bound form of the isolated protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$,3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either LRSG or its target molecule to facilitate separation of complexed from uncomplexed forms of one or both of the proteins, as well as to accommodate automation of the assay. Binding of a test compound to a LRSG protein, or interaction of a LRSG protein with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/LRSG fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or LRSG protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of LRSG binding or activity determined using standard techniques.

Other techniques for immobilizing proteins on matrices can also be used in the screening assays of the invention. For example, either a LRSG protein or a LRSG target molecule can be immobilized utilizing conjugation of biotin and streptavidin. Biotinylated LRSG protein or target molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with LRSG protein or target molecules but which do not interfere with binding of the LRSG protein to its target molecule can be derivatized to the wells of the plate, and unbound target or LRSG protein trapped in the wells by antibody conjugation. Methods for detecting such complexes, in addition to those described above for the GST-immobilized complexes, include immunodetection of complexes using antibodies reactive with the LRSG protein or target molecule, as well as enzyme-linked assays which rely on detecting an enzymatic activity associated with the LRSG protein or target molecule.

In another embodiment, modulators of LRSG expression are identified in a method wherein a cell is contacted with a candidate compound and the expression of LRSG mRNA or protein in the cell is determined. The level of expression of LRSG mRNA or protein in the presence of the candidate compound is compared to the level of expression of LRSG mRNA or protein in the absence of the candidate compound. The candidate compound can then be identified as a modulator of LRSG expression based on this comparison. For example, when expression of LRSG mRNA or protein is greater (statistically significantly greater) in the presence of the candidate compound than in its absence, the candidate compound is identified as a stimulator of LRSG mRNA or protein expression. Alternatively, when expression of LRSG mRNA or protein is less (statistically significantly less) in the presence of the candidate compound than in its absence, the candidate compound is identified as an inhibitor of LRSG mRNA or protein expression. The level of LRSG mRNA or protein expression in the cells can be determined by methods described herein for detecting LRSG mRNA or protein.

In yet another aspect of the invention, the LRSG proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with LRSG ("LRSG-binding proteins" or "LRSG-bp") and are involved in LRSG activity. Such LRSG-binding proteins are also likely to be involved in the propagation of signals by the LRSG proteins or LRSG targets as, for example, downstream elements of a LRSG-mediated signaling pathway. Alternatively, such LRSG-binding proteins are likely to be LRSG inhibitors.

The two-hybrid system is based on the modular nature of most transcription factors, which consist of separable DNA-binding and activation domains. Briefly, the assay utilizes two different DNA constructs. In one construct, the gene that codes for a LRSG protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a LRSG-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the LRSG protein.

This invention further pertains to novel agents identified by the above-described screening assays and to processes for producing such agents by use of these assays. Accordingly, in one embodiment, the present invention includes a compound or agent obtainable by a method comprising the steps of any one of the aformentioned screening assays (e.g., cell-based assays or cell-free assays). For example, in one embodiment, the invention includes a compound or agent obtainable by a method comprising contacting a cell which expresses a LRSG target molecule with a test compound and the determining the ability of the test compound to bind to, or modulate the activity of, the LRSG target molecule. In another embodiment, the invention includes a compound or agent obtainable by a method comprising contacting a cell which expresses a LRSG target molecule with a LRSG protein or biologically-active portion thereof, to form an assay mixture, contacting the assay mixture with a test compound, and determining the ability of the test compound to interact with, or modulate the activity of, the LRSG target molecule. In another embodiment, the invention includes a compound or agent obtainable by a method comprising contacting a LRSG protein or biologically active portion thereof with a test compound and determining the ability of the test compound to bind to, or modulate (e.g., stimulate or inhibit) the activity of, the LRSG protein or biologically active portion thereof. In yet another embodiment, the present invention included a compound or agent obtainable by a method comprising contacting a LRSG protein or biologically active portion thereof with a known compound which binds the LRSG protein to form an assay mixture, contacting the assay mixture with a test compound, and determining the ability of the test compound to interact with, or modulate the activity of the LRSG protein.

Accordingly, it is within the scope of this invention to further use an agent identified as described herein in an appropriate animal model. For example, an agent identified as described herein (e.g., a LRSG modulating agent, an antisense LRSG nucleic acid molecule, a LRSG-specific antibody, or a LRSG-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

The present inventon also pertains to uses of novel agents identified by the above-described screening assays for diagnoses, prognoses, and treatments as described herein. Accordingly, it is within the scope of the present invention to use such agents in the design, formulation, synthesis, manufacture, and/or production of a drug or pharmaceutical composition for use in diagnosis, prognosis, or treatment, as described herein. For example, in one embodiment, the present invention includes a method of synthesizing or producing a drug or pharmaceutical composition by reference to the structure and/or properties of a compound obtainable by one of the above-described screening assays. For example, a drug or pharmaceutical composition can be synthesized based on the structure and/or properties of a compound obtained by a method in which a cell which expresses a LRSG target molecule is contacted with a test compound and the ability of the test compound to bind to, or modulate the activity of, the LRSG target molecule is determined. In another exemplary embodiment, the present invention includes a method of synthesizing or producing a drug or pharmaceutical composition based on the structure and/or properties of a compound obtainable by a method in which a LRSG protein or biologically active portion thereof is contacted with a test compound and the ability of the test compound to bind to, or modulate (e.g., stimulate or inhibit) the activity of, the LRSG protein or biologically active portion thereof is determined.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the LRSG nucleotide sequences, described herein, can be used to map the location of the LRSG genes on a chromosome. The mapping of the LRSG sequences to chromosomes is an important first step in correlating these sequences with genes associated with disease.

Briefly, LRSG genes can be mapped to chromosomes by preparing PCR primers (preferably 15–25 bp in length) from the LRSG nucleotide sequences. Computer analysis of the LRSG sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the LRSG sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio P. et al. (1983) *Science* 220:919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the LRSG nucleotide sequences to design oligonucleotide primers, sublocalization can be achieved with panels of fragments from specific chromosomes. Other mapping strategies which can similarly be used to map a 9o, 1p, or 1v sequence to its chromosome include in situ hybridization(described in Fan, Y. et al. (1990) *PNAS,* 87:6223–27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature,* 325:783–787.

Moreover, differences in the DNA sequences between individuals affected and unaffected with a disease associated with the LRSG gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The LRSG sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the LRSG nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The LRSG nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1, can comfortably provide positive individual identification with a panel of perhaps 10 to 1,000 primers which each yield a noncoding amplified sequence of 100 bases. If predicted coding sequences, such as those in SEQ ID NO:3 are used, a more appropriate number of primers for positive individual identification would be 500–2,000.

If a panel of reagents from LRSG nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of Partial LRSG Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1 are particularly appropriate for this use as greater numbers of polymorphisms occur in the noncoding regions, making it easier to differentiate individuals using this technique. Examples of polynucleotide reagents include the LRSG nucleotide sequences or portions thereof, e.g., fragments derived from the noncoding regions of SEQ ID NO:1, having a length of at least 20 bases, preferably at least 30 bases.

The LRSG nucleotide sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such LRSG probes can be used to identify tissue by species and/or by organ type.

In a similar fashion, these reagents, e.g., LRSG primers or probes can be used to screen tissue culture for contamination (i.e. screen for the presence of a mixture of different types of cells in a culture).

C. Predictive Medicine:

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining LRSG protein and/or nucleic acid expression as well as LRSG activity, in the context of a biological sample (e.g., blood, serum, cells, tissue) to thereby determine whether an individual is afflicted with a disease or disorder, or is at risk of developing a disorder, associated with aberrant LRSG expression or activity. The invention also provides for prognostic (or predictive) assays for determining whether an individual is at risk of developing a disorder associated with LRSG protein, nucleic acid expression or activity. For example, mutations in a LRSG gene can be assayed in a biological sample. Such assays can be used for prognostic or predictive purpose to thereby phophylactically treat an individual prior to the onset of a disorder characterized by or associated with LRSG protein, nucleic acid expression or activity.

Another aspect of the invention pertains to monitoring the influence of agents (e.g., drugs, compounds) on the expression or activity of LRSG in clinical trials.

These and other agents are described in further detail in the following sections.

1. Diagnostic Assays

An exemplary method for detecting the presence or absence of LRSG protein or nucleic acid in a biological sample involves obtaining a biological sample from a test subject and contacting the biological sample with a compound or an agent capable of detecting LRSG protein or nucleic acid (e.g., mRNA, genomic DNA) that encodes LRSG protein such that the presence of LRSG protein or nucleic acid is detected in the biological sample. A preferred agent for detecting LRSG mRNA or genomic DNA is a labeled nucleic acid probe capable of hybridizing to LRSG mRNA or genomic DNA. The nucleic acid probe can be, for example, a full-length LRSG nucleic acid, such as the nucleic acid of SEQ ID NO:1 (or that of SEQ ID NO:3, or the DNA insert of the plasmid deposited with ATCC as Accession Number 98695, or a portion thereof), such as an oligonucleotide of at least 15, 30, 50, 100, 250 or 500 nucleotides in length and sufficient to specifically hybridize under stringent conditions to LRSG mRNA or genomic DNA. Other suitable probes for use in the diagnostic assays of the invention are described herein.

A preferred agent for detecting LRSG protein is an antibody capable of binding to LRSG protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect LRSG mRNA, protein, or genomic DNA in a biological sample in vitro as well as in vivo. For example, in vitro techniques for detection of LRSG mRNA include Northern hybridizations and in situ hybridizations. In vitro techniques for detection of LRSG protein include enzyme linked immunosorbent assays (ELISAs), Western blots, immunoprecipitations and immunofluorescence. In vitro techniques for detection of LRSG genomic DNA include Southern hybridizations. Furthermore, in vivo techniques for detection of LRSG protein include introducing into a subject a labeled anti-LRSG antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting LRSG protein, mRNA, or genomic DNA, such that the presence of LRSG protein, mRNA or genomic DNA is detected in the biological sample, and comparing the presence of LRSG protein, mRNA or genomic DNA in the control sample with the presence of LRSG protein, mRNA or genomic DNA in the test sample.

The invention also encompasses kits for detecting the presence of LRSG in a biological sample. For example, the kit can comprise a labeled compound or agent capable of detecting LRSG protein or mRNA in a biological sample; means for determining the amount of LRSG in the sample; and means for comparing the amount of LRSG in the sample with a standard. The compound or agent can be packaged in a suitable container. The kit can further comprise instructions for using the kit to detect LRSG protein or nucleic acid.

2. Prognostic Assays

The diagnostic methods described herein can furthermore be utilized to identify subjects having or at risk of developing a disease or disorder associated with aberrant LRSG expression or activity. For example, the assays described herein, such as the preceding diagnostic assays or the following assays, can be utilized to identify a subject having or at risk of developing a disorder associated with LRSG protein, nucleic acid expression or activity such as prostate cancer. Alternatively, the prognostic assays can be utilized to identify a subject having or at risk for developing prostate cancer. Thus, the present invention provides a method for identifying a disease or disorder associated with aberrant LRSG expression or activity in which a test sample is obtained from a subject and LRSG protein or nucleic acid (e.g, mRNA, genomic DNA) is detected, wherein the presence of LRSG protein or nucleic acid is diagnostic for a subject having or at risk of developing a disease or disorder associated with aberrant LRSG expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant LRSG expression or activity. For example, such methods can be used to determine whether a subject can be effectively treated with an agent for prostate cancer. Thus, the present invention provides methods for determining whether a subject can be effectively treated with an agent for a disorder associated with aberrant LRSG expression or activity in which a test sample is obtained and LRSG protein or nucleic acid expression or activity is detected (e.g., wherein the abundance of LRSG protein or nucleic acid expression or activity is diagnostic for a subject that can be administered the agent to treat a disorder associated with aberrant LRSG expression or activity.)

The methods of the invention can also be used to detect genetic alterations in a LRSG gene, thereby determining if a subject with the altered gene is at risk for a disorder characterized by an aberrant proliferative response. In preferred embodiments, the methods include detecting, in a sample of cells from the subject, the presence or absence of a genetic alteration characterized by at least one of an alteration affecting the integrity of a gene encoding a LRSG-protein, or the mis-expression of the LRSG gene. For example, such genetic alterations can be detected by ascertaining the existence of at least one of 1) a deletion of one or more nucleotides from a LRSG gene; 2) an addition of one or more nucleotides to a LRSG gene; 3) a substitution of one or more nucleotides of a LRSG gene, 4) a chromosomal rearrangement of a LRSG gene; 5) an alteration in the level of a messenger RNA transcript of a LRSG gene, 6) aberrant modification of a LRSG gene, such as of the methylation pattern of the genomic DNA, 7) the presence of a non-wild type splicing pattern of a messenger RNA transcript of a LRSG gene, 8) a non-wild type level of a LRSG-protein, 9) allelic loss of a LRSG gene, and 10) inappropriate post-translational modification of a LRSG-protein. As described herein, there are a large number of assay techniques known in the art which can be used for detecting alterations in a LRSG gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *PNAS* 91:360–364), the latter of which can be particularly useful for detecting point mutations in the LRSG-gene (see Abravaya et al. (1995) *Nucleic Acids Res* .23:675–682). This method can include the steps of collecting a sample of cells from a patient, isolating nucleic acid (e.g., genomic, mRNA or both) from the cells of the sample, contacting the nucleic acid sample with one or more primers which specifically hybridize to a LRSG gene under conditions such that hybridization and amplification of the LRSG-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., 1990, Proc. Natl.

Acad. Sci. USA 87:1874–1878), transcriptional amplification system (Kwoh, D. Y. et al., 1989, Proc. Natl. Acad. Sci. USA 86:1173–1177), Q-Beta Replicase (Lizardi, P. M. et all, 1988, Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a LRSG gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in LRSG can be identified by hybridizing a sample and control nucleic acids, e.g., DNA or RNA, to high density arrays containing hundreds or thousands of oligonucleotides probes (Cronin, M. T. et al. (1996) *Human Mutation* 7: 244–255; Kozal, M. J. et al. (1996) *Nature Medicine* 2: 753–759), For example, genetic mutations in LRSG can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential ovelapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the LRSG gene and detect mutations by comparing the sequence of the sample LRSG with the corresponding wild-type (control) sequence. Examples of sequencing reactions include those based on techniques developed by Maxim and Gilbert ((1977) *PNAS* 74:560) or Sanger ((1977) *PNAS* 74:5463). It is also contemplated that any of a variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the LRSG gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes of formed by hybridizing (labeled) RNA or DNA containing the wild-type LRSG sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl Acad Sci USA* 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in LRSG cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a LRSG sequence, e.g., a wild-type LRSG sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in LRSG genes. For example, single strand conformation polymorphism (SSCP) may be used to detect differences in electrophoretic mobility between mutant and wild type nucleic acids (Orita et al. (1989) *Proc Natl. Acad. Sci USA:*86:2766, see also Cotton (1993) *Mutat Res* 285:125–144; and Hayashi (1992) *Genet Anal Tech Appl* 9:73–79). Single-stranded DNA fragments of sample and control LRSG nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6: 1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a LRSG gene.

Furthermore, any cell type or tissue in which LRSG is expressed may be utilized in the prognostic assays described herein.

3. Monitoring of Effects During Clinical Trials

Monitoring the influence of agents (e.g., drugs, compounds) on the expression or activity of a LRSG protein (e.g., modulation of angiogenesis or of an inflammatory response) an be applied not only in basic drug screening, but also in clinical trials. For example, the effectiveness of an agent determined by a screening assay as described herein to increase LRSG gene expression, protein levels, or upregulate LRSG activity, can be monitored in clinical trials of subjects exhibiting decreased LRSG gene expression, protein levels, or downregulated LRSG activity. Alternatively, the effectiveness of an agent determined by a screening assay to decrease LRSG gene expression, protein levels, or downregulate LRSG activity, can be monitored in clinical trials of subjects exhibiting increased LRSG gene expression, protein levels, or upregulated LRSG activity. In such clinical trials, the expression or activity of a LRSG gene, and preferably, other genes that have been implicated in, for example, a proliferative disorder can be used as a "read out" or markers of the phenotype of a particular cell.

For example, and not by way of limitation, genes, including LRSG, that are modulated in cells by treatment with an agent (e.g., compound, drug or small molecule) which modulates LRSG activity (e.g., identified in a screening assay as described herein) can be identified. Thus, to study the effect of agents on proliferative disorders, for example, in a clinical trial, cells can be isolated and RNA prepared and analyzed for the levels of expression of LRSG and other genes implicated in the proliferative disorder, respectively.

The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of LRSG or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of expression of a LRSG protein, mRNA, or genomic DNA in the preadministration sample; (iii) obtaining one or more post-administration samples from the subject; (iv) detecting the level of expression or activity of the LRSG protein, mRNA, or genomic DNA in the post-administration samples; (v) comparing the level of expression or activity of the LRSG protein, mRNA, or genomic DNA in the pre-administration sample with the LRSG protein, mRNA, or genomic DNA in the post administration sample or samples; and (vi) altering the administration of the agent to the subject accordingly. For example, increased administration of the agent may be desirable to increase the expression or activity of LRSG to higher levels than detected, i.e., to increase the effectiveness of the agent. Alternatively, decreased administration of the agent may be desirable to decrease expression or activity of LRSG to lower levels than detected, i.e. to decrease the effectiveness of the agent. According to such an embodiment, LRSG expression or activity may be used as an indicator of the effectiveness of an agent, even in the absence of an observable phenotypic response.

D. Methods of Treatment:

The present invention provides for both prophylactic and therapeutic methods of treating a subject at risk of (or susceptible to) a disorder or having a disorder associated with aberrant LRSG expression or activity. With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the LRSG molecules of the present invention or LRSG modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant LRSG expression or activity, by administering to the subject a LRSG or an agent which modulates LRSG expression or at least one LRSG activity. Subjects at risk for a disease which is caused or contributed to by aberrant LRSG expression or activity can be identified by, for example, any or a combination of diagnostic or prognostic assays as described herein. Administration of a prophylactic agent can occur prior to the manifestation of symptoms characteristic of the LRSG aberrancy, such that a disease or disorder is prevented or, alternatively, delayed in its progression. Depending on the type of LRSG aberrancy, for example, a LRSG, LRSG agonist or LRSG antagonist agent can be used for treating the subject. The appropriate agent can be determined based on screening assays described herein. The prophylactic methods of the present invention are further discussed in the following subsections.

2. Therapeutic Methods

Another aspect of the invention pertains to methods of modulating LRSG expression or activity for therapeutic purposes. Accordingly, in an exemplary embodiment, the modulatory method of the invention involves contacting a cell with a LRSG or agent that modulates one or more of the activities of LRSG protein activity associated with the cell. An agent that modulates LRSG protein activity can be an agent as described herein, such as a nucleic acid or a protein, a naturally-occurring target molecule of a LRSG protein, a LRSG antibody, a LRSG agonist or antagonist, a peptidomimetic of a LRSG agonist or antagonist, or other small molecule. In one embodiment, the agent stimulates one or more LRSG activities. Examples of such stimulatory agents include active LRSG protein and a nucleic acid molecule encoding LRSG that has been introduced into the cell. In another embodiment, the agent inhibits one or more LRSG activites. Examples of such inhibitory agents include antisense LRSG nucleic acid molecules, anti-LRSG antibodies, and LRSG inhibitors. These modulatory methods can be performed in vitro (e.g., by culturing the cell with the agent) or, alternatively, in vivo (e.g, by administering the agent to a subject). As such, the present invention provides methods of treating an individual afflicted with a disease or disorder characterized by aberrant expression or activity of a LRSG protein or nucleic acid molecule. In one embodiment, the method involves administering an agent (e.g., an agent identified by a screening assay described herein), or combination of agents that modulates (e.g., upregulates or downregulates) LRSG expression or activity. In another embodiment, the method involves administering a LRSG protein or nucleic acid molecule as therapy to compensate for reduced or aberrant LRSG expression or activity.

Stimulation of LRSG activity is desirable in situations in which LRSG is abnormally downregulated and/or in which increased LRSG activity is likely to have a beneficial effect. For example, stimulation of LRSG activity is desirable in situations in which a LRSG is downregulated and/or in which increased LRSG activity is likely to have a beneficial effect. Likewise, inhibition of LRSG activity is desirable in situations in which LRSG is abnormally upregulated and/or in which decreased LRSG activity is likely to have a beneficial effect.

3. Pharmacogenomics

The LRSG molecules of the present invention, as well as agents, or modulators which have a stimulatory or inhibitory effect on LRSG activity (e.g., LRSG gene expression) as identified by a screening assay described herein can be administered to individuals to treat (prophylactically or therapeutically) disorders (e.g, prostate cancer) associated with aberrant LRSG activity. In conjunction with such treatment, pharmacogenomics (i.e., the study of the relationship between an individual's genotype and that individual's response to a foreign compound or drug) may be considered. Differences in metabolism of therapeutics can icad to severe toxicity or therapeutic failure by altering the relation between dose and blood concentration of the pharmacologically active drug. Thus, a physician or clinician may consider applying knowledge obtained in relevant pharmacogenomics studies in determining whether to administer a LRSG molecule or LRSG modulator as well as tailoring the dosage and/or therapeutic regimen of treatment with a LRSG molecule or LRSG modulator.

Pharmacogenomics deals with clinically significant hereditary variations in the response to drugs due to altered drug disposition and abnormal action in affected persons. See e.g., Eichelbaum, M., *Clin Exp Pharmacol Physiol,* 1996, 23(10–11):983–985 and Linder, M. W., *Clin Chem,* 1997, 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (antimalarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drugs target is known (e.g., a LRSG protein or LRSG receptor of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C 19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., a LRSG molecule or LRSG modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a LRSG molecule or LRSG modulator, such as a modulator identified by one of the exemplary screening assays described herein.

This invention is further illustrated by the following examples which should not be construed as limiting. The contents of all references, patents and published patent applications cited throughout this application are incorporated herein by reference.

EXAMPLES

Example 1

Identification And Characterization of human LRSG-1 cDNA

In this example, th e identification and characterization of the gene encoding human LRSG-1 (also referred to as "TANGO 124") is described.

Isolation of the human LRSG-1 cDNA

The invention is based, at least in part, on the discovery of a human gene encoding a novel leucine-rich repeat containing protein, referred to herein as LRSG-1. Human astrocytes (obtained from Clonetics Corporation; San Diego, Calif.) were expanded in culture with Astrocyte Growth Media (AGM; Clonetics) according to the recommendations of the supplier. When the cells reached ~80–90% confluence, they were stimulated with 200 units/ml Interleukin 1-Beta (Boehringer Mannheim) and cycloheximide (CHI; 40 micrograms/ml) for 4 hours. Total RNA was isolated using the RNeasy Midi Kit (Qiagen; Chatsworth, Calif. ), and the poly A+ fraction was further purified using Oligotex beads (Qiagen).

Three micrograms of poly A+RNA were used to synthesize a cDNA library using the Superscript cDNA Synthesis kit (Gibco BRL; Gaithersburg, Md.). Complementary DNA was directionally cloned into the expression plasmid pMET7 using the SalI and NotI sites in the polylinker to construct a plasmid library. Transformants were picked and grown up for single-pass sequencing. Additionally, astrocyte cDNA was ligated into the SalI/NotI sites of the ZipLox vector (Gibco BRL) for construction of a lambda phage cDNA library. A clone jthxe016d10) that encoded a protein with limited homology to decorin, insulin-like growth factor binding protein and biglycan was identified. Full sequencing of the clone demonstrated that it contained an ~2.8 kb insert with a single large open reading frame predicted to encode a 673 amino acid transmembrane protein.

The nucleotide sequence encoding the human LRSG-1 protein is shown in FIG. 1 and is set forth as SEQ ID NO: 1. The full length protein encoded by this nucleic acid is comprised of about 673 amino acids and has the amino acid sequence shown in FIG. 1 and set forth as SEQ ID NO:2. The coding portion (open reading frame) of SEQ ID NO:1 is set forth as SEQ ID NO:3. Clone jthxe016d10, comprising the entire coding region of human LRSG-1 has been deposited with the American Type Culture Collection (ATCC), Manassas. Va., on Mar. 12, 1998 as Accession No. 98695.

Notable features of the the human LRSG-1 protein include a signal peptide (about amino acids 1–23 of SEQ ID NO:2), a transmembrane domain (about amino acids 576–599 of SEQ ID NO:2) an EGF-like domain (about amino acids 409–441) and a fibronectin type III-like domain (about amino acids 460–535 of SEQ ID NO:2). Th human LRSG-1 protein further includes a leucine-rich region (about amino acids 77–309 of SEQ ID NO:2) which includes at least 7 leucine-rich repeats (about amino acids 77–309, 101–123, 125–147, 149–171, 217–238, 240–263, and 289–309 of SEQ ID NO:2).

Analysis of Human LRSG-1

A BLAST search (Altschul et al. (1990) *J. Mol. Biol.* 215:403) of the nucleotide and protein sequences of human LRSG-1 has revealed that LRSG-1 has structural similarities with both platelet glycoprotein V precursor (GPV) (SwisProt Accession No. P40197) and insulin-like growth factor binding protein complex acid labile chain precursor (ALS) (SwisProt Accession No. O02833). Each of these proteins is a leucine-rich repeat containing protein although LRSG-1 shares no greater than 30% identity with any of these LRR-containing proteins. An alignment of human LRSG-1 and the above-described proteins is presented in FIG. 2.

Expression of LRSG-1

The expression of LRSG-1 was analyzed using Northern blot hybridization. A 579 base pair (bp) DNA fragment from the N-terminal portion of the coding region was generated using PCR for use as a probe. The DNA was radioactively labeled with $^{32}$p-dCTP using the Prime-It-kit (Stratagene, La Jolla, Calif.) according to the instructions of the supplier. Filters containing human mRNA (Multi-Tissue Northern I and Multi-Tissue Northern II from Clontech, Palo Alto, Calif.) were probed in ExpressHyb hybridization solution (Clontech) and washed at high stringency according to manufacturer's recommendations.

Results of Northern blot hybridization indicate that LRSG-1 is expressed as an approximately 3.0 kilobase transcript in all tissues (spleen, thymus, prostate, testes, ovary, small intestine, colon, heart, brain, placenta, lung, liver, skeletal muscle, kidney and pancreas) with the exception of peripheral blood leukocytes. The highest levels of LRSG-1 were found in placenta, kidney and testis.

Equivalents

Those skilled in the art will recognize, or be able to ascertain using no more than routine experimentation, many equivalents to the specific embodiments of the invention described herein. Such equivalents are intended to be encompassed by the following claims.

What is claimed:

1. An isolated nucleic acid molecule comprising a nucleotide sequence which encodes a polypeptide comprising the amino acid sequence of SEQ ID NO:2 or amino acid sequence of SEQ ID NO:2 without amino acids 1 to 23.

2. An isolated nucleic acid molecule comprising a nucleotide sequence which encodes a polypeptide comprising an amino acid sequence encoded by the DNA insert of the plasmid deposited with ATCC as Accession Number 98695.

3. An isolated nucleic acid molecule comprising a nucleotide sequence which encodes a mature polypeptide encoded by the DNA insert of the plasmid deposited with ATCC as Accession Number 98695.

4. An isolated nucleic acid molecule comprising a nucleotide sequence which encodes an allelic variant of a polypeptide comprising the amino acid sequence of SEQ ID NO:2, wherein the nucleotide sequence hybridizes to a nucleic acid molecule comprising SEQ ID NO:1 under conditions of incubation at 45° C. in 6.0×SSC followed by washing in 0.2×SSC/0.1% SDS at 50–65° C.

5. An isolated nucleic acid molecule comprising a nucleotide sequence which encodes an allelic variant of a polypeptide comprising the amino acid sequence of SEQ ID NO:2, wherein the nucleotide sequence hybridizes to a nucleic acid molecule comprising SEQ ID NO:3 under conditions of incubation at 45° C. in 6.0×SSC followed by washing in 0.2×SSC/0.1% SDS at 50–65° C.

6. An isolated nucleic acid molecule comprising the nucleotide sequence of SEQ ID NO:1 or the complement thereof.

7. An isolated nucleic acid molecule comprising the nucleotide sequence of SEQ ID NO:3 or the complement thereof.

8. An isolated nucleic acid molecule comprising the nucleotide sequence of the DNA insert of the plasmid deposited with ATCC as Accession Number 98695, or the complement thereof.

9. An isolated nucleic acid molecule comprising a nucleotide sequence encoding a polypeptide consisting of the amino acid sequence of SEQ ID NO:2, or the complement thereof.

10. An isolated nucleic acid molecule comprising a nucleotide sequence encoding a polypeptide consisting of the amino acid sequence of SEQ ID NO: 2 without amino acids 1 to 23, or the complement thereof.

11. An isolated nucleic acid molecule comprising a nucleotide sequence encoding a polypeptide consisting of the amino acid sequence encoded by the DNA insert of the plasmid deposited with ATCC as Accession Number 98695, or the complement thereof.

12. An isolated nucleic acid molecule comprising a nucleotide sequence encoding a polypeptide consisting of the amino acid sequence of the mature polypeptide encoded by the DNA insert of the plasmid deposited with ATCC as Accession Number 98695, or the complement thereof.

13. An isolated nucleic acid molecule consisting of the nucleotide sequence of SEQ ID NO:1 or the complement thereof.

14. An isolated nucleic acid molecule consisting of the nucleotide sequence of SEQ ID NO:3 or the complement thereof.

15. An isolated nucleic acid molecule consisting of the nucleotide sequence of the DNA insert of the plasmid deposited with ATCC as Accession Number 98695 or the complement thereof.

16. An isolated nucleic acid molecule consisting of the coding region of the nucleotide sequence of the DNA insert of the plasmid deposited with ATCC as Accession Number 98695 or the complement thereof.

17. The nucleic acid molecule as in any of the preceding claims which further comprises vector nucleic acid sequences.

18. A host cell which contains the nucleic acid molecule of claim 17.

19. A host cell which contains the nucleic acid molecule as in any one of claims 1–16.

20. The host cell of claim 18 which is a mammalian host cell.

21. The host cell of claim 19 which is a mammalian host cell.

* * * * *